US009459089B2

(12) United States Patent
Ganton et al.

(10) Patent No.: US 9,459,089 B2
(45) Date of Patent: Oct. 4, 2016

(54) METHOD, DEVICES AND SYSTEMS FOR DETECTING AN ATTACHMENT OF AN ELECTRONIC PATCH

(71) Applicant: QUALCOMM Incorporated, San Diego, CA (US)

(72) Inventors: Robert Bruce Ganton, San Diego, CA (US); Robert Scott Ballam, Eatons Hill (AU)

(73) Assignee: QUALCOMM Incorporated, San Diego, CA (US)

( * ) Notice: Subject to any disclaimer, the term of this patent is extended or adjusted under 35 U.S.C. 154(b) by 148 days.

(21) Appl. No.: 14/459,996

(22) Filed: Aug. 14, 2014

(65) Prior Publication Data

US 2015/0292856 A1 Oct. 15, 2015

Related U.S. Application Data

(60) Provisional application No. 61/977,390, filed on Apr. 9, 2014.

(51) Int. Cl.
*G01R 27/26* (2006.01)
*G01B 7/02* (2006.01)
(Continued)

(52) U.S. Cl.
CPC ............. *G01B 7/023* (2013.01); *A61B 5/6833* (2013.01); *A61B 5/6844* (2013.01);
(Continued)

(58) Field of Classification Search
CPC .......... G01B 7/023; G01B 7/22; G01B 7/08; G01B 7/044; A61B 5/6833; A61B 5/6844; A61B 2560/0209; A61B 2560/028; A61B 2562/0257
USPC ............ 324/658, 671, 662–663; 340/870.37, 340/530, 540, 545.4, 562; 600/365
See application file for complete search history.

(56) References Cited

U.S. PATENT DOCUMENTS 5,109,842 A * 5/1992 Adinolfi ............... A61N 1/3962
600/375
6,023,970 A * 2/2000 Blaine ................... G01F 23/284
73/290 R
(Continued)

FOREIGN PATENT DOCUMENTS

GB WO 2014005974 A1 * 1/2014 ............. A61B 5/165
WO 2010104952 A2 9/2010
(Continued)

OTHER PUBLICATIONS

International Search Report and Written Opinion—PCT/US2015/024967—ISA/EPO—Oct. 13, 2015.
(Continued)

*Primary Examiner* — Patrick Assouad
*Assistant Examiner* — Sean Curtis
(74) *Attorney, Agent, or Firm* — The Marbury Law Group, PLLC

(57) ABSTRACT

An electronic sensor patch includes a capacitive sensor configured to detect when the electronic sensor patch is applied to a patient. A processor may be powered down for a predetermined time interval in response to determining that the electronic patch is not in close proximity to a body. The electronic sensor patch may be activated in response to determining that the electronic patch is in close proximity to the body. The capacitance sensor may be used to determine whether the electronic sensor patch is in close proximity to a body by measuring capacitance of the capacitance sensor, comparing the measured capacitance to a threshold, and determining that the electronic sensor patch is in close proximity to a body in response to the measured capacitance of the capacitance sensor being more than the threshold.

64 Claims, 10 Drawing Sheets

(51) Int. Cl.
*A61B 5/00* (2006.01)
*H03K 17/955* (2006.01)

(52) U.S. Cl.
CPC . *A61B 2560/028* (2013.01); *A61B 2560/0209* (2013.01); *A61B 2562/0257* (2013.01); *H03K 17/955* (2013.01); *H03K 2217/94042* (2013.01)

(56) References Cited

U.S. PATENT DOCUMENTS

| | | | | |
|---|---|---|---|---|
| 6,239,601 B1* | 5/2001 | Weinstein | ............... | B64D 15/20 324/649 |
| 7,187,960 B2* | 3/2007 | Abreu | ............... | A61B 5/01 374/E13.002 |
| 7,222,239 B2* | 5/2007 | Smith | ............... | G07C 9/00111 713/185 |
| 7,725,149 B2* | 5/2010 | Peyser | ............... | A61B 5/14521 600/346 |
| 8,147,446 B2* | 4/2012 | Yodfat | ............... | A61M 5/14248 604/131 |
| 8,229,535 B2* | 7/2012 | Mensinger | ............... | A61B 5/7445 600/345 |
| 8,328,420 B2* | 12/2012 | Abreu | ............... | A61B 5/0008 374/163 |
| 8,340,776 B2* | 12/2012 | Doron | ............... | A61N 1/3787 600/485 |
| 8,444,578 B2* | 5/2013 | Bourget | ............... | A61B 5/0002 600/595 |
| 8,591,455 B2* | 11/2013 | Mensinger | ............... | A61B 5/7445 600/301 |
| 8,710,993 B2* | 4/2014 | Hayter | ............... | A61B 5/14532 340/521 |
| 8,747,348 B2* | 6/2014 | Yodfat | ............... | A61M 5/14248 604/131 |
| 8,798,761 B2* | 8/2014 | Doron | ............... | A61B 5/0031 607/60 |
| 8,810,391 B2* | 8/2014 | Cok | ............... | G06K 19/0717 324/337 |
| 8,818,450 B2* | 8/2014 | Caballero | ............... | H04B 1/3838 455/13.4 |
| 8,823,490 B2* | 9/2014 | Libbus | ............... | A61B 5/0006 340/6.1 |
| 8,849,379 B2* | 9/2014 | Abreu | ............... | A61B 5/0008 374/121 |
| 8,925,392 B2* | 1/2015 | Esposito | ............... | A61B 5/1036 73/862.01 |
| 8,930,203 B2* | 1/2015 | Kiaie | ............... | A61B 5/14532 705/2 |
| 9,020,572 B2* | 4/2015 | Mensinger | ............... | A61B 5/7445 600/345 |
| 2005/0277841 A1* | 12/2005 | Shennib | ............... | A61B 5/0444 600/511 |
| 2006/0030782 A1* | 2/2006 | Shennib | ............... | A61B 5/0402 600/509 |
| 2009/0030285 A1* | 1/2009 | Andersen | ............... | A61B 5/6843 600/300 |
| 2009/0105605 A1* | 4/2009 | Abreu | ............... | A61B 5/0008 600/549 |
| 2010/0198034 A1* | 8/2010 | Thomas | ............... | A61B 5/14532 600/365 |
| 2011/0213225 A1 | 9/2011 | Bernstein et al. | | |
| 2011/0213325 A1* | 9/2011 | Gabrielii | ............... | A61F 13/496 604/385.3 |
| 2012/0108917 A1* | 5/2012 | Libbus | ............... | A61B 5/0006 600/301 |
| 2012/0245447 A1* | 9/2012 | Karan | ............... | A61B 5/14532 600/365 |
| 2013/0079605 A1* | 3/2013 | Bandaru | ............... | A61B 5/6833 600/310 |
| 2013/0110415 A1* | 5/2013 | Davis | ............... | A42B 3/046 702/41 |
| 2013/0127627 A1* | 5/2013 | Hayter | ............... | A61B 5/14532 340/657 |
| 2013/0132416 A1* | 5/2013 | Hayter | ............... | G06F 19/32 707/758 |
| 2013/0184547 A1* | 7/2013 | Taub | ............... | A61B 5/14532 600/365 |
| 2013/0245388 A1* | 9/2013 | Rafferty | ............... | A61B 8/4416 600/301 |
| 2013/0289424 A1* | 10/2013 | Brockway | ............... | A61B 5/0402 600/509 |
| 2014/0012094 A1* | 1/2014 | Das | ............... | A61B 5/08 600/300 |
| 2014/0088454 A1* | 3/2014 | Mack | ............... | A61B 5/11 600/553 |
| 2014/0200426 A1* | 7/2014 | Taub | ............... | A61B 5/14532 600/347 |
| 2015/0150505 A1* | 6/2015 | Kaskoun | ............... | A61B 5/6833 600/300 |
| 2015/0292856 A1* | 10/2015 | Ganton | ............... | A61B 5/6833 324/671 |

FOREIGN PATENT DOCUMENTS

WO   WO 2010104952 A2 * 9/2010 ........... A61B 5/0002
WO      2014005974 A1   1/2014

OTHER PUBLICATIONS

Presse A.F., "Scientists have Created an Incredible Patient-Monitoring Device that is the Size of a Band-Aid," Business Insider, Mar. 2014, [Retrieved date on May 12, 2014], Retrieved from the Internet < URL : http://www. businessinsider.in/Scientists-Have-Created-An-Incredible-Patient-Monitoring-Device-That-Is-The-Size-Of-A-Band-Aid/articleshow/33003421.cms >, 3 pages.
Partial International Search Report—PCT/US2015/024967—ISAEPO—Jun. 23, 2015.

* cited by examiner

METHOD, DEVICES AND SYSTEMS FOR DETECTING AN ATTACHMENT OF AN ELECTRONIC PATCH

RELATED APPLICATIONS

This application claims the benefit of priority to U.S. Provisional Patent Application No. 61/977,390 filed Apr. 9, 2014, the entire contents of which are hereby incorporated by reference for all purposes.

BACKGROUND

Electronic sensors or patches can be used for biometric and biomedical monitoring. While electronic patches provide some degree of convenience, challenges remain.

Challenges in implementing electronic patches include reliability, connection quality, data security, integrity and fault tolerance, integration of diverse sensor technology, managing delay of real-time measurements, comfort, longevity and other challenges. Challenges may further include enabling electronic patches to reliably operate at the desired time. Challenges may further include reliable assembly of electronic patches without compromising operational readiness.

SUMMARY

The various embodiments provide a simple, low-cost capacitance sensor configured to detect when an electronic patch is attached to a patient in order to activate the patch. An embodiment method of activating an electronic sensor patch configured to be applied to a patient may include using the capacitance sensor to determine whether the electronic sensor patch is in close proximity to a body. To detect whether the patch is applied to a body, a processor of the electronic patch may briefly apply a voltage to the capacitance sensor and determine whether there has been a change in capacitance. In order to conserve battery power, the electronic sensor patch may power down to a low-power mode for a predetermined time interval in response to determining that the electronic patch is not in close proximity to a body. In response to determining that the electronic patch is in close proximity to the body, such as by detecting a change in capacitance, the processor may activate the electronic sensor patch so that it may initiate on-body operations.

Using a capacitance sensor to determine whether the electronic sensor patch is in close proximity to a body may include energizing the capacitance sensor upon expiration of the predetermined time interval, measuring capacitance of the capacitance sensor, comparing the measured capacitance of the capacitance sensor to a threshold, and determining that the electronic sensor patch is in close proximity to a body in response to the measured capacitance of the capacitance sensor equaling or exceeding the threshold. Energizing the capacitance sensor may include applying to the capacitance sensor one of a voltage from a voltage source, and a constant current from a constant current source.

A further embodiment method may include executing a manufacturing mode by the processor of the electronic patch in response to connection to a battery power source, in which the capacitance sensor is not activated. The manufacturing mode may be implemented for a predetermined period of time, such as measured by a timer, after which the electronic patch enters a monitoring or shelf mode in which the capacitive sensor is energized periodically. The manufacturing mode prevents the capacitive sensor from activating the electronic patch due to handling during manufacture and test. A further embodiment method may include determining a duration that the processor has been in the shelf mode, and transmitting an indication of the determined duration that the processor has been in the shelf mode in response to activation of the electronic sensor patch.

A further embodiment method for deactivating an electronic sensor patch configured to be applied to a patient may include activating an active life timer, determining whether the active life timer has expired, and deactivating the electronic sensor patch in response to determining that the active life timer has expired.

A further embodiment method may include using a capacitance sensor to determine whether the electronic sensor patch is in close proximity to a body, activating the electronic sensor patch in response to determining that the electronic sensor patch is in close proximity to the body, and executing an on-body operations mode to perform one or more on-body operations in response to activating the electronic sensor patch. In an embodiment method, the one or more on-body operations may include a sensing operation, and/or a communication operation.

In a further embodiment method, in response to determining that the active life timer has expired, the processor may send a deactivation signal indicating that the electronic patch will be deactivated. Deactivating the electronic sensor patch in response to the active life timer expiring may include purging data stored in memory, such as by disconnecting power to the memory, and/or overwriting data stored in the memory.

In various embodiments, an embodiment electronic sensor patch may include one or more of a battery, a capacitance sensor, a memory, one or more medical or biological sensors, a radio module, and a processor configured with processor-executable instructions to perform operations of the methods described above. An embodiment sensor patch may include means for performing operations of the methods described above. An embodiment includes a non-transitory processor-readable medium storing processor-executable instructions configured to cause a processor of an electronic sensor patch to perform operations of the methods described above.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of various embodiments.

DETAILED DESCRIPTION

Figure 1A:
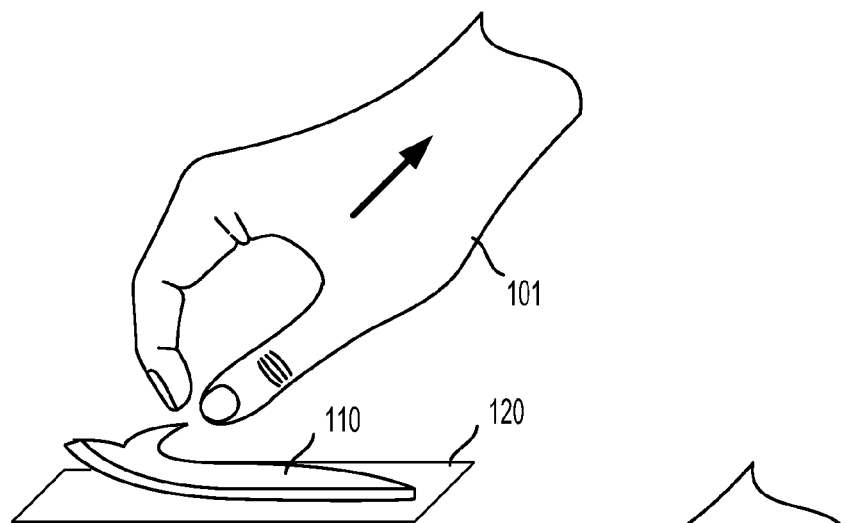
FIG. 1A is a diagram illustrating an embodiment electronic patch being removed from a packaging base or insulator.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims or embodiments.

As used herein, the terms "electronic patch" and "electronic sensor patch" may be used interchangeably herein and refer to a medical device in the form of an electronic patch that can include sensors for sensing or measuring one or more detectable physical phenomena or quantities. An electronic sensor patch may be configured to transmit signals indicative of a measurement or sensed state, condition or quantity. The signals generated by a sensor may be processed to measure the one or more detectable physical quantities based on a correlation between the signal and the underlying physical quantity. Non-limiting examples of sensors that may be implemented in an electronic sensor patch include temperature sensors, pulse sensors, electric field sensors (e.g., electroencephalograph sensors), moisture sensors, liquid flow sensors, magnetic sensors, piezoelectric sensors, pressure sensors, optical sensors, chemical sensors (e.g., blood glucose sensors), and other bio-medical sensors.

In conventional electronic patches, an on/off switch is generally not provided for various reasons. For example, an on/off switch may be inadvertently turned off defeating the diagnostic function of the electronic patch. Alternatively, electronic patches may generally be packaged in the "on" position. As a result, challenges may include maintaining battery life when patches are being stored.

The various embodiments overcome the drawbacks of existing and proposed electronic patches by providing an electronic patch having an attachment detection device. The electronic sensor may be configured to detect certain timing conditions and the condition of the attachment detection device in order to determine various operational modes. The electronic patch may be provided with an attachment detection device for determining when the electronic patch is attached to a patient. The electronic sensor may be assembled such that a battery or power source may be inserted into the electronic patch during the assembly process having a known maximum duration. Upon application of power to the electronic patch during assembly, a processor or controller may enter a factory mode or manufacturing mode in which the electronic patch may be configured, tested and sealed. Upon application of power, the processor may be configured to begin to determine whether the electronic patch is still within an established duration for the factory mode. The duration of the factory or manufacturing mode may established based on knowledge of the typical time, a maximum time, or an average time to assemble, configure, test, package, seal and provide the packaged electronic patch into a distribution channel. The processor may determine whether the factory mode is still active by checking a counter or timer that is driven by a clock. The electronic patch may be sealed during assembly such that the electronic patch is powered. In some embodiments, the factory mode may include various modes for testing, such as testing at full power and functionality, testing low power operations, and/or testing a low power clock.

When the factory mode timer expires, the electronic patch is assumed to be packaged and ready for purchase and use. The electronic patch may enter a shelf mode, which may also be referred to as a detection mode. The shelf mode, may be a low power mode in which a low power clock may be configured to run, such as to track a timer. The electronic patch may be energized at certain brief intervals, such as when the timer expires, to detect whether the electronic patch has been placed on a subject. The electronic patch may include an attachment detection device, which may be an attachment detector, such as touch or contact sensitive capacitance sensor, or similar circuit configured to sense when the patch is attached to a patient. Because the power consumed to detect attachment to a patient by such an attachment detection device is low and the activation time to perform this operation is very brief (on the order of a millisecond) compared to the time that the electronic patch is deenergized (on the order of several seconds), the drain on the battery is very low enabling the shelf/detection mode to be maintained for many months while leaving sufficient energy stored in the battery to power sensor operations when finally attached to a patient. The sealing materials applied to the electronic patch may provide sufficient electrical resistance to isolate the capacitance-type attachment detection device from being affected by people handling the sealed electronic patch. When the electronic patch is unsealed and attached directly to a subject, the capacitance in the capacitive circuit changes. When the electronic patch periodically activates in order to check the attachment condition, the change in capacitance from the contact causes the processor to detect a change in a parameter such as, for example, an RC time constant of the attachment detection device (e.g., an attachment detection circuit of the device).

When attachment of the electronic patch to a subject is detected (e.g., by the electronic patch processor), the electronic patch may switch from the shelf mode, which may also be referred to as a detection mode to an on-body operation mode in which a quantity sensor unit associated with the electronic patch may be activated and used to measure biometric quantities (e.g., temperature, pulse rate, B/P, electrical fields, etc.) running on battery power.

A receiver may receive data from the electronic patch. A receiver may be a mobile computing device, an access point, or other computing device configured with suitable wireless communication circuitry including another electronic sensor.

In an embodiment, the electronic patch may be assembled during manufacture with insulating packaging such that the attachment detection device will not be inadvertently triggered when handled by humans or contacted by objects. For example, the electronic patch unit may be packaged as a peel off adhesive patch. The electronic patch may be peeled off from an insulating base that prevents the attachment detection circuit from being accidentally triggered. The electronic patch may be configured to be removed, peeled off, or detached from the insulating base. The electronic patch may further include an adhesive substrate, which may be affixed to a bottom surface of the electronic patch. The adhesive substrate may securely attach the electronic patch to the insulating base when packaged. The adhesive substrate may also securely attach the electronic patch to a body of a subject, such as to the skin of a patient or wearer, or other surface when removed from the packaging and placed into operation.

In various embodiments, the electronic patch may be configured to measure different physical or physiological parameters, such as temperature, blood pressure, electrophysiology signals (e.g., electrocardiogram (EKG) and electroencephalogram signals), muscle movements, blood oxygenation level, and other physical or physiological parameters.

In various embodiments, the electronic patch may be configured to further detect that an active life of the sensor is expired. A processor of the electronic patch may conduct active on-body operations and also may check a timer value for the active life of the electronic patch. Alternatively, an active life, remaining active life, and/or end-of-life for the electronic patch may be determined by measuring a battery voltage. The determination of the end-of-life may be factored into determining a suitable amount of time for any terminal processing that should be completed before the patch is deactivated. When the active life has expired, the electronic patch may be deactivated and further actions such as the deletion of any stored values may be taken.

FIG. 1A shows a diagram illustrating an electronic patch being removed from a packaging base or insulator. In various embodiments, an electronic patch 110 may be configured to be flexible and resilient so that placement and removal of the electronic patch from an insulating base 120 does not damage the electronic patch 110. A user 101 may grip the electronic patch 110, such as by a pull tab, and apply a removal force to remove the electronic patch 110 from the insulated base 120. The removal force may be sufficient to overcome the adhesive force supplied by the adhesive that attaches to the electronic patch 110. The insulated base 120 may prevent spurious detection in a capacitance sensor.

Figure 1B:
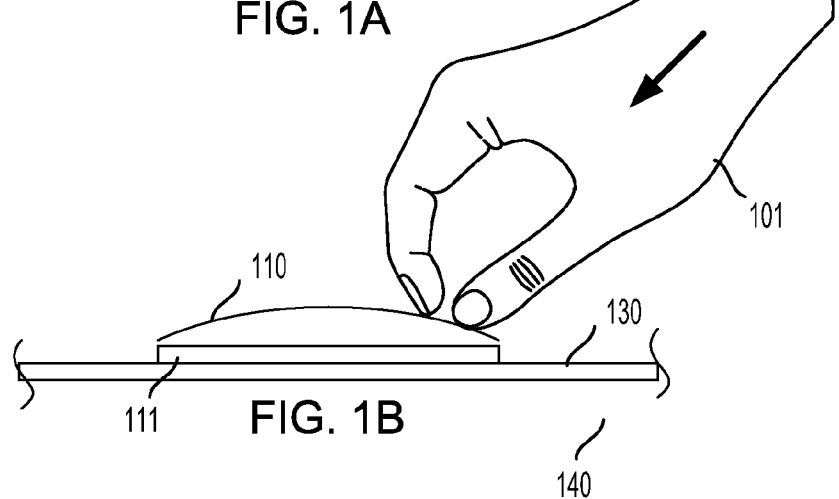
FIG. 1B is a diagram illustrating an embodiment electronic patch being placed on a subject.

In various embodiments such as illustrated in FIG. 1B, the electronic patch 110 may be placed on a subject 140, such as on a skin surface 130 of the subject 140. An adhesive layer 111 may be used to affix the electronic patch 110 to the skin surface 130. The adhesive layer 111 may further allow the electronic patch 110 to be affixed to the insulating base 120. In the various embodiments, when the active life of the electronic patch 110 has not expired, the electronic patch may be placed back on the adhesive base 120, whereupon the electronic patch may re-enter a low-power shelf mode.

In various embodiments, the electronic patch 110 may be configured to issue an alarm if the electronic patch 110 has been attached to the subject 140 and removed after a period of time that is prior to a specified removal time. Such a premature removal of the electronic patch 110 could indicate non-compliance or non-adherence to a treatment or monitoring protocol or may indicate other anomalies, error conditions, or failures. Thus, one or more additional modes may be provided. For example, upon removal, the electronic patch 110 may return to a detection or shelf mode. Alternatively, the electronic patch 110 may enter an alarm mode if prematurely removed after being applied. Other modes are possible depending on the use case of the electronic patch 110. In one or all of the additional cases, the electronic patch may be configured to communicate the patch removal, alarm condition, anomaly, or error to a receiving device. In some embodiments, when a premature removal of the electronic patch 110 is detected, a reset and/or memory purge operation may be conducted to delete data, such as private patient data, that may be stored in a memory within or associated with the electronic patch 110. Operations for purging data from memory, including overwriting data and removing power to volatile memory, are described below with reference to FIG. 6. In the event that another electronic patch is placed on the patient, data may be uploaded to the memory of the new patch from server or a hub, such as when a communication with the replacement electronic patch 110 is established.

Figure 1C:
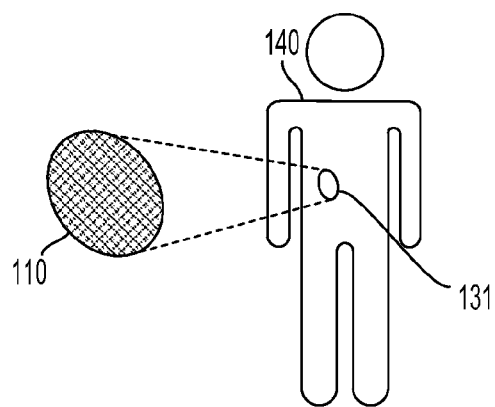
FIG. 1C is a diagram illustrating an embodiment electronic patch placement relative to a body of a subject.

In various embodiments, the electronic patch 110 may be placed on the subject 140 at a particular location 131 as illustrated in FIG. 1C. The position of the location 131 may facilitate a biometric quantity reading for a sensor unit associated with the electronic patch 110.

Figure 2A:
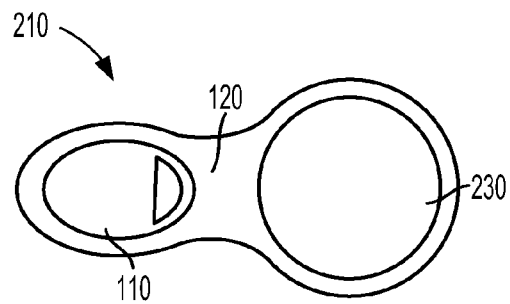
FIG. 2A-FIG. 2C are diagrams illustrating alternative embodiments of a multi-sensor unit with an electronic control unit and removable electronic patches.
Figure 2B:
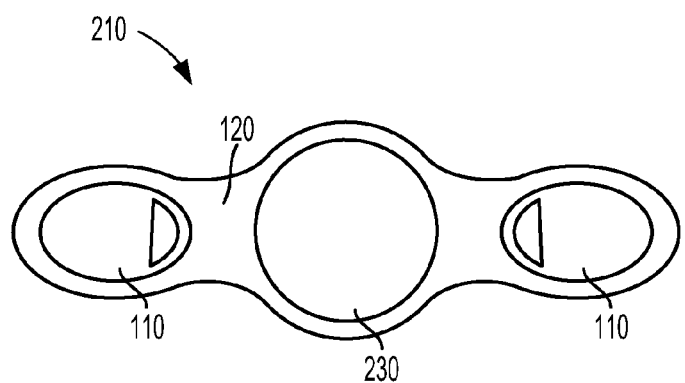
Figure 2C:
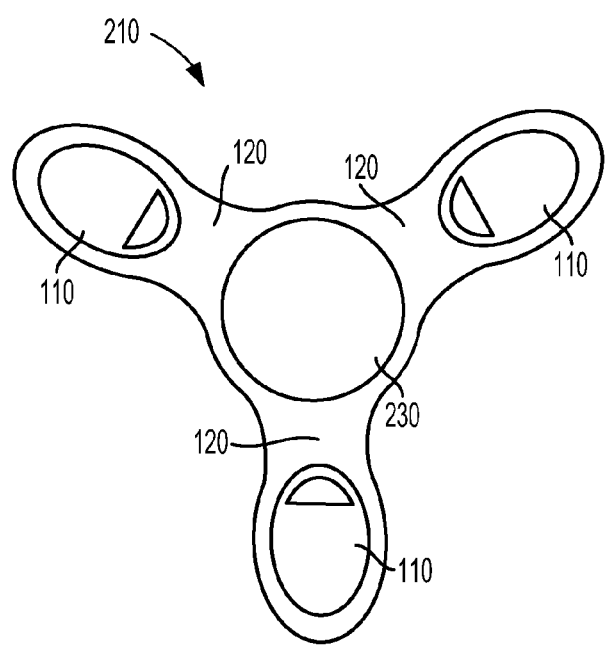

In some embodiments, the electronic patch 110 may be provided as a sensor array unit 210 having an electronic hub unit 230. In such an array, any number of electronic patches 110 may be included in a sensor array unit 210. For example, the sensor array unit 210 may include a single electronic patch 110 as illustrated in FIG. 2A, two electronic patches 110 as illustrated in FIG. 2B, or three electronic patches 110 as illustrated in FIG. 2C. In some embodiments (not shown), the number of electronic patches 110 of the sensor array unit 210 may be more than three and may be limited only by the available space on insulating base 120 and the size of the electronic patches 110. In some embodiments, the sensor array unit 210 may be equipped with a large number of electronic patches 110, some or all of which may be used in-place forming a measurement array that may communicate with the hub unit 230 or other receiver device, and provide improved accuracy in the measurement of the physical or physical or physiological parameter. Though used in-place, in some embodiments, the electronic patches 110 may be configured to detect attachment to a patient as described herein. Detection may be possible both in place, when one or more of the electronic patches 110 are removed from the insulating base 120 and placed on a body of a patient. In other embodiments, the sensor array unit 210 may have a separate attachment detection circuit, which may be used to activate the on-body mode for the individual electronic patches 110. Persons skilled in the art will appreciate that in some embodiments the one or more electronic patches 110 need not be integrated on to a single form factor. Rather, the electronic patches can be attached separately to the patient and still be configured to communicate with hub unit 230 or other receiver device.

Figure 3A:
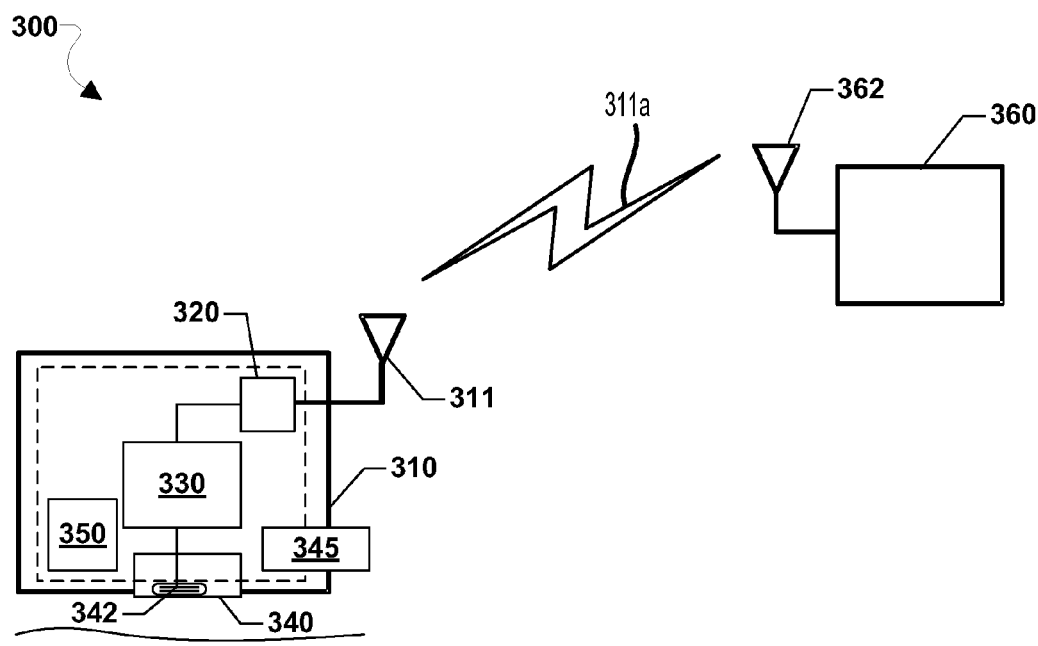
FIG. 3A is a component block diagram illustrating example wireless interconnections of an electronic patch having an attachment detector and a receiver for a remote sensing configuration.

A components block diagram of an embodiment system 300 of an electronic patch 310 and receiver 360 is shown in FIG. 3A. The electronic patch 310 may include an antenna 311, a radio module 320, a processor 330, an attachment detection device 340, one or more sensors 345, and a power supply 350. The attachment detection device 340 may include a sensing unit 342, which may be a capacitive sensing unit. As shown by the dotted line, some or all the components of the electronic patch 310 may be encapsulated or sealed within the electronic patch 310 to provide environmental protection. In some embodiments, the electronic patch 310 may be configured to operate in a variety of environmental conditions including wet conditions. Some or all of the components of the electronic patch 310, such as the processor 330 and the radio module 320, may be provided as individual components or may be integrated into a single device. The components of the electronic patch 310 may be sealed or encapsulated to allow operation when at least partially submerged in water or other liquids.

The receiver 360 may include an antenna 362 and other components (not shown) such as a processor, RF module, memory and other components. The receiver 360 may be configured to receive sensor data from the electronic patch 310 during application of the electronic patch 310 to a subject and operation of the electronic patch 310.

When the electronic patch 310 is within range of the receiver 360, a wireless communication link 311a may be established between the electronic patch 310 and the receiver 360 through an antenna 362. The wireless communication link 311a may allow the electronic patch 310 to transfer information to the receiver 360, such as sensor data or readings from the one or more of sensors 345 associated with the electronic patch 110.

Figure 3B:
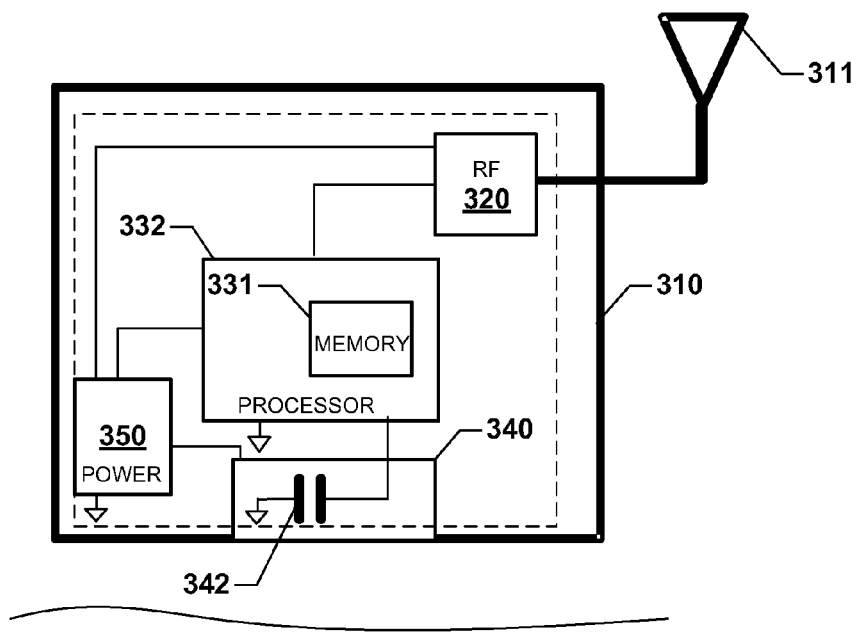
FIG. 3B is a component block diagram further illustrating an attachment detector of an electronic patch.

A component block diagram of the electronic patch 310 of the embodiment system 300 is shown in FIG. 3B. As described above, the electronic patch 310 may include an antenna 311 and a radio (RF) module 320. The RF module 320 may be a transmit-only, or a transceiver module that includes various components to enable, in connection with the processor 330 to conduct one-way or two-way radio frequency communication. For example, the RF module may include base band, intermediate and transmit frequency modules and encoders. The RF module 320 may operate in one or more of a number of radio frequency bands depending on the type of communications supported by the configuration of the receiver 360.

The processor 330 may be configured with a processing unit 332 and a memory 331. The processing unit 332 may be a single or multi-core processor, which may be general purpose or specifically adapted for use in the electronic sensor 310. The memory 331 of the processor 330 may be volatile or non-volatile memory or a combination thereof. The processor 330, the attachment detection device 340, and the RF module 320 and any other electronic components of the electronic patch 310 may be powered by a power supply 350. The power supply 350 may typically be a battery, such as a lithium-ion battery or other long life battery. Alternatively, the power supply 350 may be another type of power supply such as an energy harvesting power supply, which may include a solar power supply.

Figure 3C:
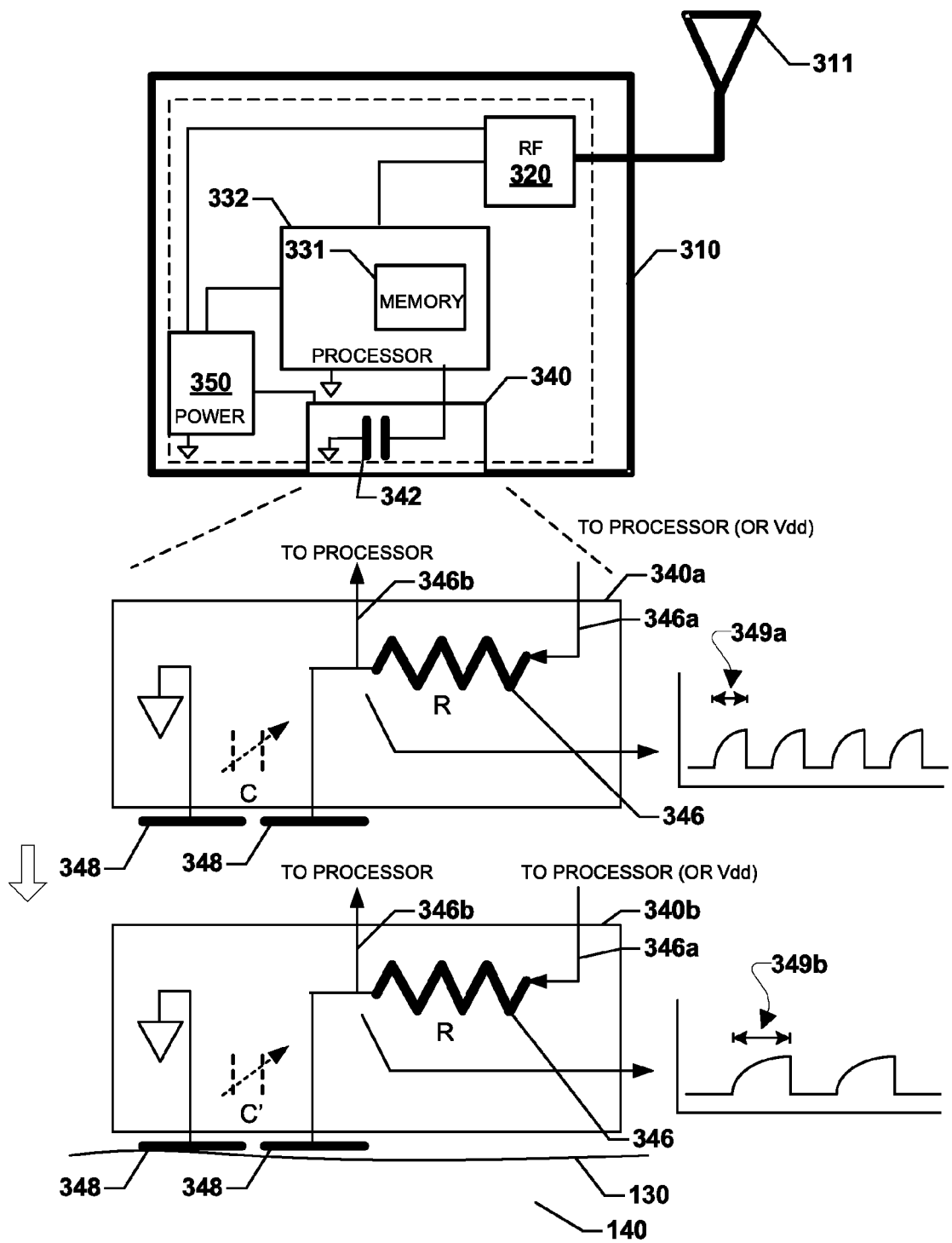
FIG. 3C is a component block diagram and circuit and timing diagrams illustrating an embodiment attachment detector of an electronic patch in a non-detected condition and detected condition.
Figure 3D:
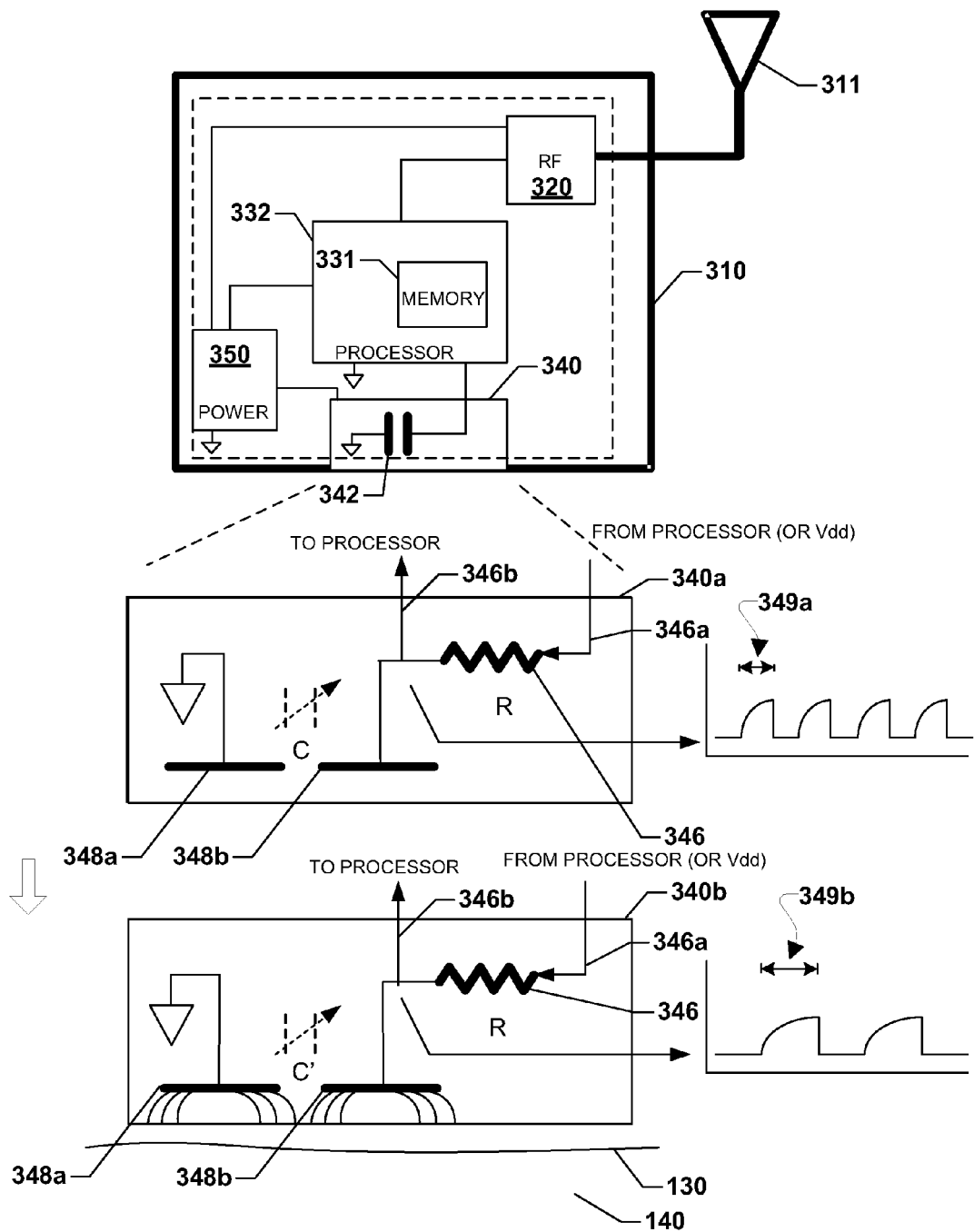
FIG. 3D is a component block diagram and circuit and timing diagrams further illustrating an embodiment attachment detector of an electronic patch in a non-detected condition and detected condition.

In the various embodiments, the attachment detection device 340 may be configured to detect when the electronic patch 310 is applied to a subject as further illustrated in FIG. 3C and FIG. 3D. The attachment detection device 340 may include sensing pads 348, which have an effective capacitance (represented as capacitance 342) and a resistance 346. In some embodiments the capacitance 342 and the resistance 346 may form at least a portion of a capacitive sensing unit as described herein. For ease of illustration, capacitance 342 is illustrated in the figure in various places as a capacitor. However, the effective capacitance C and C' can form the variable capacitances, which may be used to detect the attachment condition. In some embodiments, the sensing pads 348 may each have an external surface that is not encased with the other components of the electronic patch 310. In some embodiments, the resistance 346 is optional, because a constant current source may drive the capacitive sense circuit. Also, in some embodiments, the resistance 346 and the sensing pads 348 may be other components that are functionally equivalent to capacitors and resistors or that provide similar responses to a touch signal applied to the sensing pads 348. The illustrated embodiments are meant to be exemplary and non-limiting and show examples of circuits that may be used to achieve a detection function. Thus, other circuits may be used to detect that the electronic patch has been applied to a subject.

In an embodiment illustrated in FIG. 3C, when the electronic patch 310 is not attached to a subject (i.e., when the sensing pads 348 are not close to or in contact with a subject), such as when the electronic patch is attached to an insulating base (e.g., insulating base 120), a signal associated with the attachment detection device 340a may have a given time constant (e.g., RC time constant) based on the values of the capacitance 342 and the resistance 346. Such a signal may be generated by stimulating the circuit with a given pulse or signal from either a voltage source or a constant current source. Such a signal may be applied to node 346a of the resistor 346. A response may be "read" from node 346b, which may be coupled to a pin on the processor 330. For example, a rise time 349a of such a pulse or signal may be measured by the processor 330 by reading the signal on node 346b. Alternatively, the signal may be generated internally in the processor 330 based on the time constant established by the values of the capacitance 342 and the resistance 346. Persons skilled in the art will appreciate that other approaches may also be used that take advantage of the relationship established by the values of the capacitance 342 and the resistance 346.

As illustrated in FIG. 3C, when the electronic patch is attached to the skin 130 of the subject 140 and the sensor pad 348 is close to or contacts the skin 130 of the subject 140, the effective capacitance of the capacitance 342 is changed by the electrical properties of the subject (e.g., C to C'). In response to the change in the capacitance 342 from C to C', the signal associated with the attachment detection device 340b may have a new time constant (e.g., RC' time constant) based on the new value of the capacitance 342 and the resistance 346. As described, such a signal may be generated by stimulating the circuit with a given pulse or signal applied to the node 346a and reading the response from the node 346b. For example, a rise time 349b of such a pulse or signal may be measured by the processor 330. The difference in the rise time 349a and 349b may be measured by the processor 330 and the attachment condition may be detected. While 349a and 349b are described as rise times, decay times may also be effectively used to calculate the differences in the time constants between the detected and non-detected states.

The attachment condition may be detected by comparing periodic attachment detection device 340 readings with either previous readings or stored readings that are known to correspond to non-attached condition. Depending on the values selected for R and C, the difference between the non-detected and the detected conditions may vary greatly. However, some selections for the R and C values may lead to high sensitivity for the attachment detection device 340. An attachment detection device that is configured for high sensitivity may also be more prone to providing false positive attachment determinations. Values for R and C in some embodiments may further depend on a time used to measure the RC time constant (e.g., rise time, decay time). A further consideration for the values for R and C in some embodiments can include the current consumption. Current consumption may depend directly on the applied voltage levels, measurement time, and/or other considerations. In some embodiments, in order to provide extended battery life, current consumption may be minimized while preserving detection sensitivity. As noted above, instead of including a resistor, similar results may be obtained using a constant current source to energize the capacitance 342.

As discussed, the attachment detection circuit may be configured in a number of ways to enable detecting the application of the electronic patch 310. A further example is illustrated in FIG. 3D. The attachment detection device 340 may include a pair of detection sensor electrodes 348a and 348b, which may be encapsulated with the other components of the electronic device 310. Because the electronic patch 310 may be placed on a person, exposure to a variety of elements hostile to electronics is possible, such as moisture, water, other fluids or materials, or shock from mechanical contact with devices. Therefore, encapsulation may refer to encasing components of the electronic patches in a material, such as a resin, or other material, that provides a barrier or seal protecting circuitry from environment elements. Encapsulation may further provide structural support for delicate components, such as for the purpose of holding the components in a particular placement or orientation, and for protecting the components from damage. For ease of illustration, the detection circuit may be represented in various places as a capacitance 342. However, in various embodiments, the detection sensor electrodes 348a and 348b may have an effective capacitance between them in the detected and non-detected conditions. When the attachment detection circuit 340b comes into close proximity or touches the skin 130 of the subject 140, the electric fields associated with the detection sensor electrodes 348a and 348b may be modified, which directly changes the effective capacitance from C to C'. In the present embodiment, the sensor electrodes 348a and 348b may be encapsulated and may not come into direct contact with the skin 130 of the subject 140. By being encapsulated and not coming into contact with the skin 130 of the subject 140, potential degradation of the sensor electrodes 348a and 348b may be prevented. Encapsulation may further prevent the influence on environmental factors, such as moisture, on readings provided by the sensor electrodes 348a and 348b. Further, the encapsulation material may be configured to prevent or reduce the potential for irritation of the skin 130. Thus, by preventing direct contact with the sensor electrodes 348a and 348b and the skin 130, the sensor electrodes may be protected as well as the skin 130 of the subject 140. As described such changes may be detected by comparing rise times 349a and 349b of a signal that is affected by the change in the RC time constant, from an RC time constant to an RC' time constant. While 349a and 349b are described as charge times, or rise times, decay times may also be used to calculate the differences in the time constants between the detected and non-detected states.

Figure 3E:
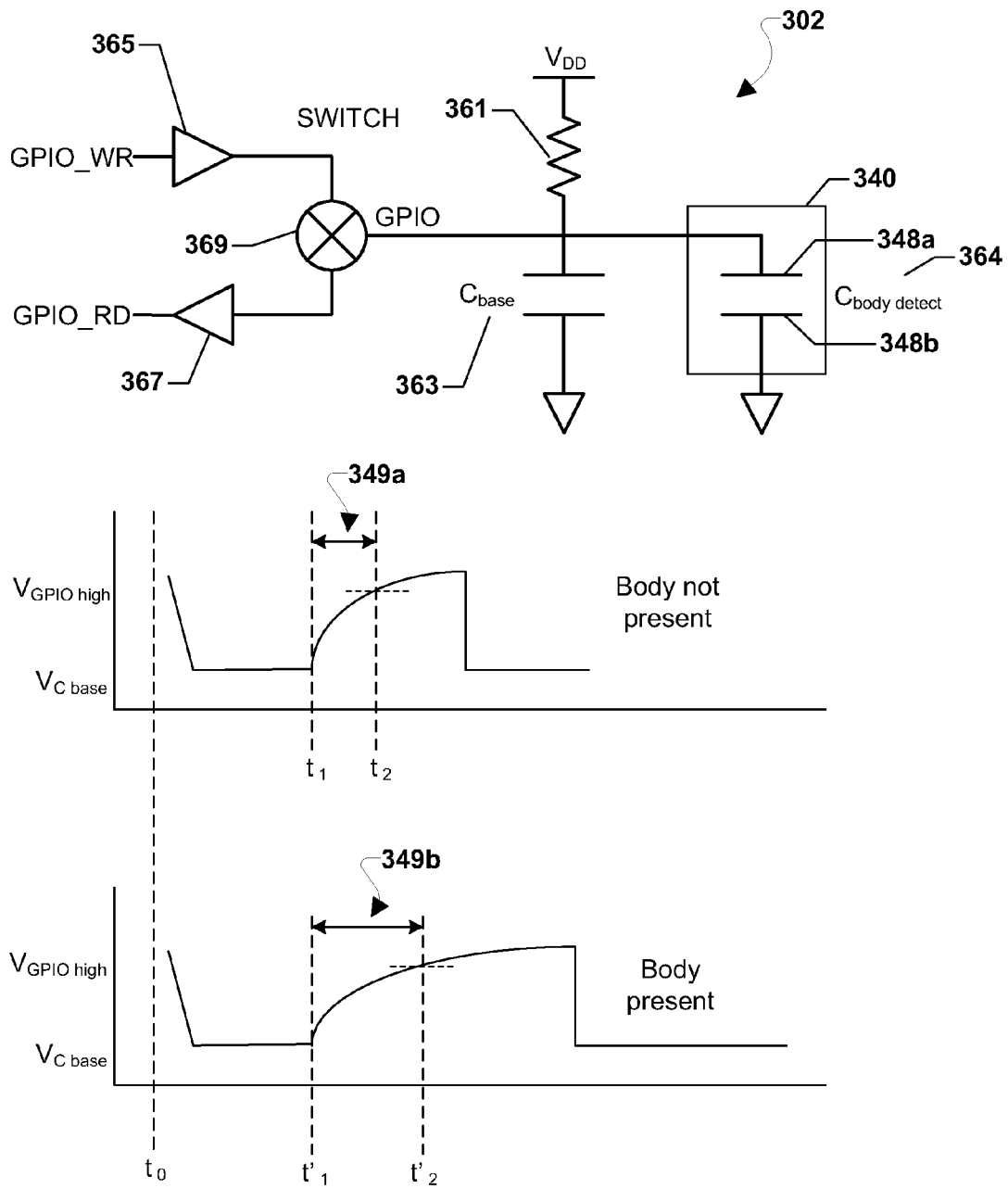
FIG. 3E includes practical circuit and timing diagrams further illustrating operation an embodiment attachment detector of an electronic patch in a non-detected condition and in a detected condition.

In some embodiments, such as an embodiment 302 as shown in FIG. 3E, a signal may be output to or "written" to the attachment detection circuit 340 or read from the attachment detection circuit 340 from a general purpose input/output (GPIO) pin of the processor 330. The output signal may charge an RC circuit of the attachment detection circuit 340, which may be composed of a resistance 361, a base capacitance $C_{base}$ 363, and a body detection capacitance $C_{body\ detect}$ 364. The body detection capacitance $C_{body\ detect}$ 364 may be composed of electrodes 348a and 348b, which in some embodiments may be a pair of plates in a folded flexible arrangement as further described with reference to FIG. 3F. The GIPO pin of the processor 330 may be an input and output pin. The GPIO pin of the processor 330 may be coupled to a switch 369 that switches the GPIO pin between input and output functions.

In an output mode, the switch 369 may be coupled to a pin driver 365. When an output signal GPIO_WR is generated by the processor 330, the output signal may be coupled through the pin driver 365 and the switch 369 to the attachment detection circuit 340.

In an input mode, the switch 369 may be coupled to a pin buffer 367 such that an input from the attachment detection circuit 340 may be read through the switch 369. Switching the state of the switch 369 may be controlled by the processor 330. For example, the processor 330 may configure the switch 365 in the output mode. The processor 330 may generate the output signal GPIO_WR and apply the signal to the attachment detection circuit 340 through the pin driver 365 and the switch 369. The output signal may be applied to the attachment detection circuit 340 to charge the attachment detection circuit 340 at the beginning of a monitoring cycle. The processor 330 may then change the switch 369 to an input mode, where the input signal GPIO—RD may be read through the pin buffer 367, the switch 369 and the attachment circuit 340. For example, the input signal GPIO_RD may enable the processor 330 to read a charge profile or time constant of the attachment detection circuit 340. Persons skilled in the art will appreciate that other configurations to apply and read signals from the attachment detection circuit 340 are possible.

In some embodiments, for example when a body is not present, the processor 330 may switch the operation of the general purpose signal line (GPIO) by applying an output signal (GPIO_WR) at a time $t_0$. The processor 330 may then switch to an input mode to receive an input signal (GPIO_RD) from the attachment detection circuit 340. The rise characteristic of the signal may be read during a charge phase or decay characteristic of the signal may be read after the charge phase. In some embodiments, at a time $t_1$ a charge period for the combined capacitances of the capacitance $C_{base}$ 363 and the body detection capacitance $C_{body\ detect}$ 340 may begin. The signal may continue to charge until a threshold value is reached, such as at time $t_2$ when a voltage $V_{GPIO\ high}$ is reached. Thus, when the charge/discharge level reaches the threshold value, time $t_2$ may be read and a time 349a between $t_1$ and $t_2$ may be measured.

In some embodiments, for example when a body is present, the processor 330 may switch the operation of the general purpose signal line (GPIO) by applying an output signal (GPIO_WR) at a time $t_0$. The processor 330 may then switch to an input mode to receive an input signal (GPIO_RD) from the attachment detection circuit 340. Alternatively, a voltage source may be applied to the node 346b as described above, and the processor may manipulate the voltage level on the node 346b by selectively toggling a pin coupled to the resistor 346 to achieve an input signal. The rise or decay characteristic of the signal may be read during a charge or discharge phase, respectively, such as on the node 346b as described herein above. In some embodiments when a body is present, at a time $t'_1$ a charge/discharge period for the combined capacitances of the capacitance $C_{base}$ 363 and the body detection capacitance $C_{body\ detect}$ 364 may begin. The presence of a body may change the capacitance of the body detection capacitance $C_{body\ detect}$ 364, having the effect of changing the combined capacitance. The signal may continue to charge or discharge until a threshold value is reached, such as a time $t'_2$ when a voltage $V_{GPIO\ high}$ is reached. When the charge or discharge level reaches the threshold value, time $t'_2$ may be read and a time 349b between $t'_1$ and $t'_2$ may be measured.

The difference in the time measurements, such as the difference between the time 349a (e.g. $t_1$ to $t_2$) and the time 349b (e.g., $t'_1$ to $t'_2$), can reflect the different capacitances between a body present and a body not present condition. This difference may thus be used to detect the presence of the body. Alternatively, the difference between time measurements $t_1$ and $t_2$ and $t'_1$ and $t'_2$ may be used to measure an effective capacitance associated with a body being present or not present. The presence of the body may indicate attachment. Alternatively, in some embodiments, two GPIO lines may be used. One GPIO line may be used for applying a signal to charge the capacitance between the electrodes 348a and 348b, such as through the resistance 361. The other GPIO line may be used to measure or read the voltage from the capacitance, such as through a direct connection to one or more of the electrodes 348a and 348b, such as the electrode 348a, which is connected to the resistance 361.

Figure 3F:
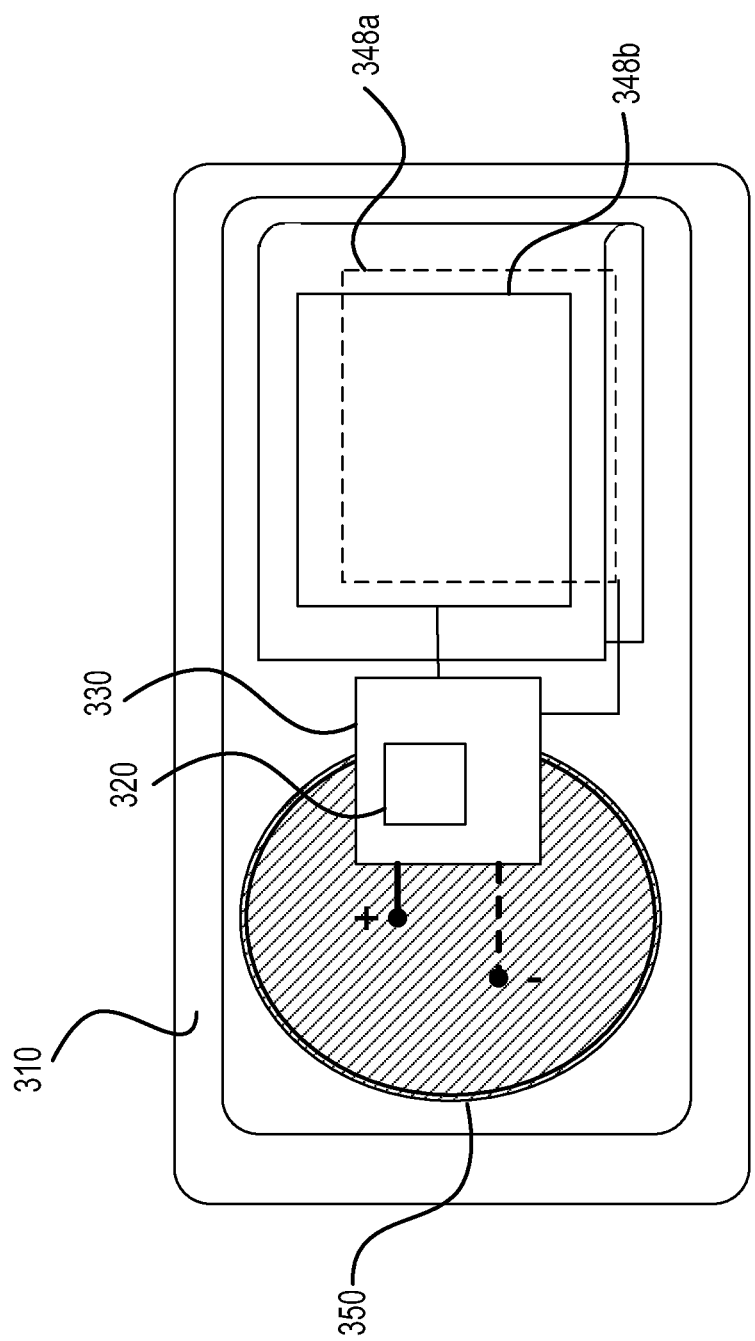
FIG. 3F is a photographic diagram illustrating a practical embodiment electronic patch including co-planar metal plates forming a capacitance attachment detector suitable for use in the various embodiments.

A practical example of an embodiment electronic patch is illustrated in FIG. 3F. An electronic patch 310 may be configured as a sealed patch, which may be removed from a package (not shown) that insulates the attachment detection portion of the patch from being activated as described hereinabove. The electronic patch 310 may include a power source 350, which may be a battery 350 in a thin flat package having positive and negative terminals (e.g., positive side, negative side). The battery 350 may be any suitable battery of sufficient power to energize various circuits associated with the electronic patch 310 over the projected life of the patch, taking into account factors such as expected shelf life. For example, the battery 350 may be a standard watch, calculator or electronic device battery. The components of the electronic patch 310 may be sealed together to prevent incursion of environmental agents of all kinds, including water, dust, bodily fluids, humidity, and other agents. The electronic patch 310 may be provided with an attachment detection device or circuit made up of the electrodes 348a and 348b, which in the illustrated embodiment may be two metal plates. The metal plates making up the electrodes 348a and 348b may be situated in a sandwich configuration (i.e. co-planar). The metal plates making up the electrodes 348a and 348b may be provided encased in a flexible material that may be folded to achieve a co-planar arrangement of the plates and may incorporate electrical connections and any supporting circuitry (e.g., flex circuit). Other components such as the processor 330, the radio module 320 including any antenna circuits, and possibly other circuits may be encased together in the electronic patch 310.

The metal plates making up the electrodes 348a and 348b may be sealed within the electronic patch 310 and positioned such that when the electronic patch is attached to a subject, the plates making up the electrodes 348a and 348b are co-planar with each other and parallel with the skin surface of the subject. Such placement provides a good electric field coupling between the skin and the plates making up the electrodes 348a and 348b to facilitate attachment detection. In some embodiments the plates making up the electrodes 348a and 348b may be configured to be coplanar and encapsulated by a media, such as an encapsulation media that has a low dielectric constant. When the plates making up the electrodes 348a and 348b are not in proximity to a body (i.e., free space) the effective capacitance will be low due to the dielectric constant of the media. During attachment, the plates making up the electrodes 348a and 348b may be placed on or very close to a body. In some embodiments, the plates making up the electrodes 348a and 348b may be separated from the body by a relatively thin adhesive layer used for attachment. During attachment, the dielectric constant may be significantly increased due to the presence of the body and, as a result, the effective capacitance may increase.

While FIGS. 3A-3F show a single capacitance sensor included in an electronic patch, in some embodiments more than one capacitance sensor may be included in the electronic patch. Including more than one capacitance sensor may be useful for some applications by providing redundancy and ensuring activation even when the entire patch is not in contact with the person's body. For example, an embodiment electronic patch that included non-electronic components may include capacitive sensors around the non-electronic components to ensure that the patch is well attached to the patient.

In the various embodiments, the electronic patch 310 may provide an advantage in that the electronic patch may be assembled and packaged as an "active" device, but one that is in a low power mode, such as during the shelf mode. The factory mode may be a transient mode that allows configuration and testing of the electronic patch 310. In the low power mode of the shelf mode, the electronic device 310 may conserve power to extend shelf life of the device. However, because the device is "active" in the low power mode of the shelf mode, the electronic patch 310 may become fully operational as soon as the device is attached.

Figure 4A:
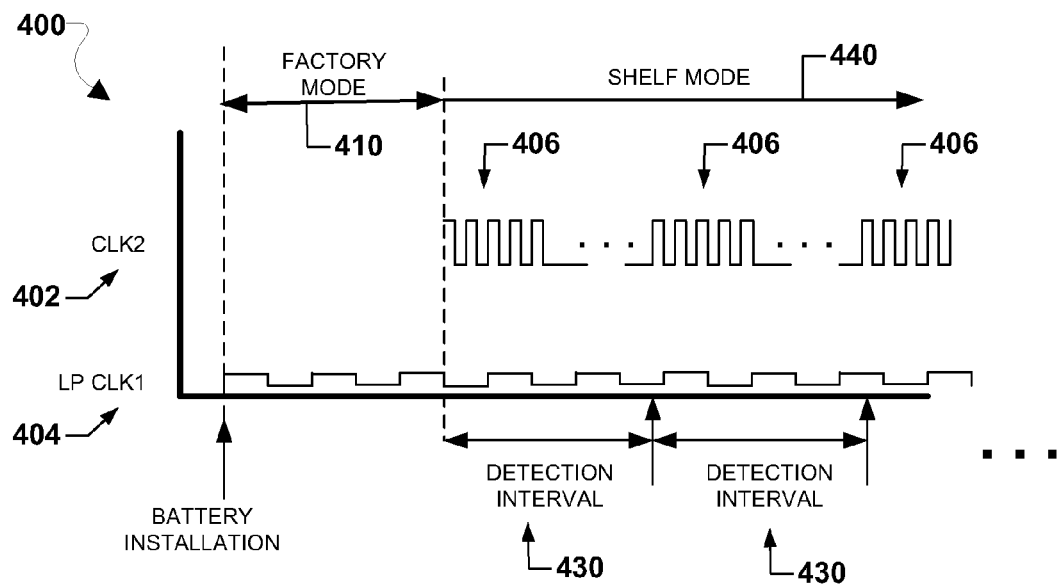
FIG. 4A is a timing diagram illustrating clock and timing conditions for various non-detected modes for an embodiment electronic patch.
Figure 4B:
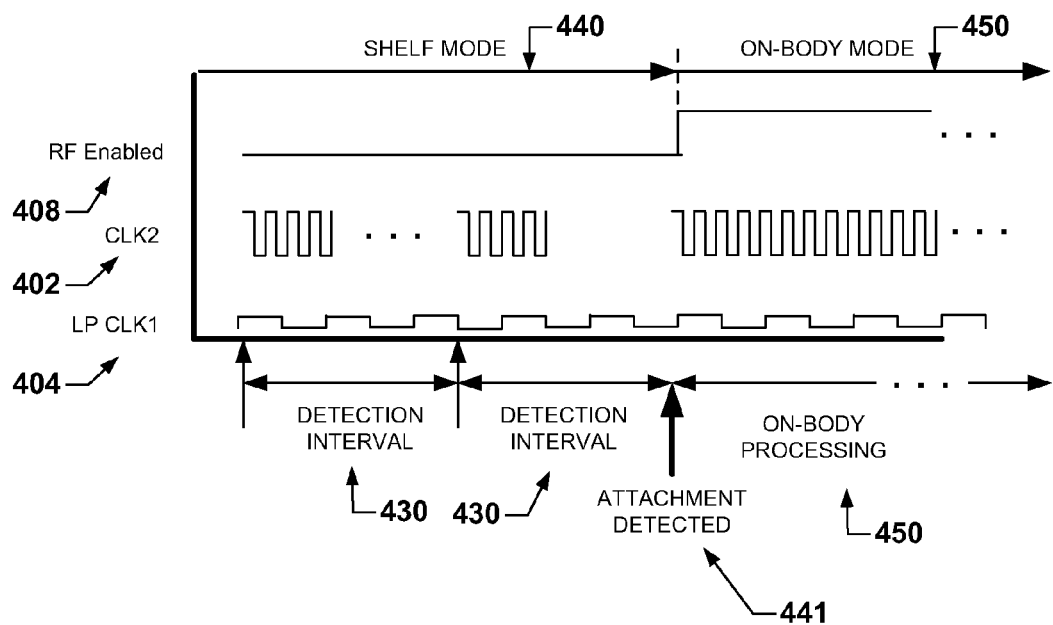
FIG. 4B is a timing diagram illustrating clock and timing conditions for various non-detected and detected modes for an embodiment electronic patch.

To accomplish mode management, an embodiment timing schedule 400 may be tracked as illustrated in FIG. 4A and 4B. Manufacturing and assembly of the electronic patch 310 may be conducted according to a known schedule. In other words, under normal operating conditions, the duration of time of each step in the manufacturing process may be known along with the maximum assembly time for the electronic patch 310.

Thus, a factory mode 410 duration may be established that represents the time from the first application of power, until the manufacturing, assembly and packaging process is complete. When the battery is installed in the electronic device 310, the processor may begin operation including operation of a low power clock (LP CLK1) 404. The LP CLK1 404 allows the processor to know the elapsed time since activation (e.g. battery installation) and to track the remaining time for the factory mode 410. The processor 330 may detect the expiration of the factory mode 410, such as by the expiration of related timers. When the factory mode 410 expires, the electronic patch 310 may transition to enter a shelf mode in which attachment detection operations are briefly performed periodically punctuated by much longer intervals in which the processor is in a low-power mode. In the shelf mode the electronic patch 310 can use the low power clock to periodically wake up to determine if the electronic patch 310 has been applied or attached.

Thus, a detection interval 430 may be established as a patient detection loop. That is, detection intervals 430 may be performed cyclically until the patch is placed on the body. The detection interval 430 may be from a few seconds to a few minutes in various embodiments. In other embodiments, the detection interval 430 may be shorter or longer. The detection interval 430 may be set in order to optimize the responsiveness of the finished patch product. For example, the detection interval 430 may be set to optimize the length of low power state to preserve battery life, while providing a relatively short sensing interval for improved responsiveness.

In embodiments, the detection interval 430 may be set in consideration of the time it takes for a patient to remove the electronic patch 310 from packaging, remove the electronic patch 310 from an insulating base 120 and apply to the skin 130 of a subject 140. Alternatively, or in addition to, the detection interval 430 may be set in consideration of the tradeoff between shelf life and detection latency. At each expiration of the patient detection loop, the processor 330, or an auxiliary processing unit, may be configured to perform a check of the attachment detection device 340, in the above described manner or other manner. In one example, a full duty cycle clock (CLK2) 402 may be enabled for a period of time sufficient to complete detection activities. The full duty cycle clock 402 may generate a full duty cycle clock signal 406. In some embodiments, the full duty cycle clock 402 may generate the full duty cycle clock signal 406 for a sufficiently short period of time to detect an attachment condition while having a minimal effect on battery power.

The patient detection loop may continue until attachment is detected, as illustrated in FIG. 4B. Upon detection, such as at time 441, the electronic patch 310 may transition into a full on-body processing mode 450. When the electronic patch 310 is in the on-body processing mode 450, sensors associated with the electronic patch 310 may be activated. Other systems such as the RF module 320 may be activated, such as by activating an enabling signal 408, by activating power rails or by other actions. When attachment has been detected, the full duty cycle clock 402 may be applied continuously or as may be called for under control of the processor 330 to accomplish sensor readings and to transmit the sensor readings to a receiver device. The full operation of the electronic patch 310 may continue while in the on-body processing mode 450. In some embodiments, the electronic patch 310 may be removed from the skin 130 of the subject 140 at which time the attachment detection device 340 may no longer detect the attachment condition. In such an example, the electronic patch 310 may re-enter a low power mode. Alternatively or additionally, the electronic patch 310 may provide an alert or notification to a receiver, such as a smart phone, cloud server, or other device indicating that the electronic patch has been removed.

In some embodiments, the electronic patch 310 may be provided with a total active life parameter, which may be influenced by quality or other factors. The total active life parameter may be in the form of a timer value, which, like other timer values described herein, may be counted down by operation of the LP CLK1 404. In some embodiments, the active life parameter may be counted down during the various modes, such as during the shelf mode and the on-body mode. When the active life timer indicates that the electronic patch 310 is reaching the end of its active life, the electronic patch may alert a user of the electronic patch 310. In some embodiments, the alert may indicate that the electronic patch 310 should be removed and replaced. If the electronic patch 310 has not been attached, the alert may indicate that the electronic patch 310 is near or at the end of its active life and therefore should not be used.

Figure 5:
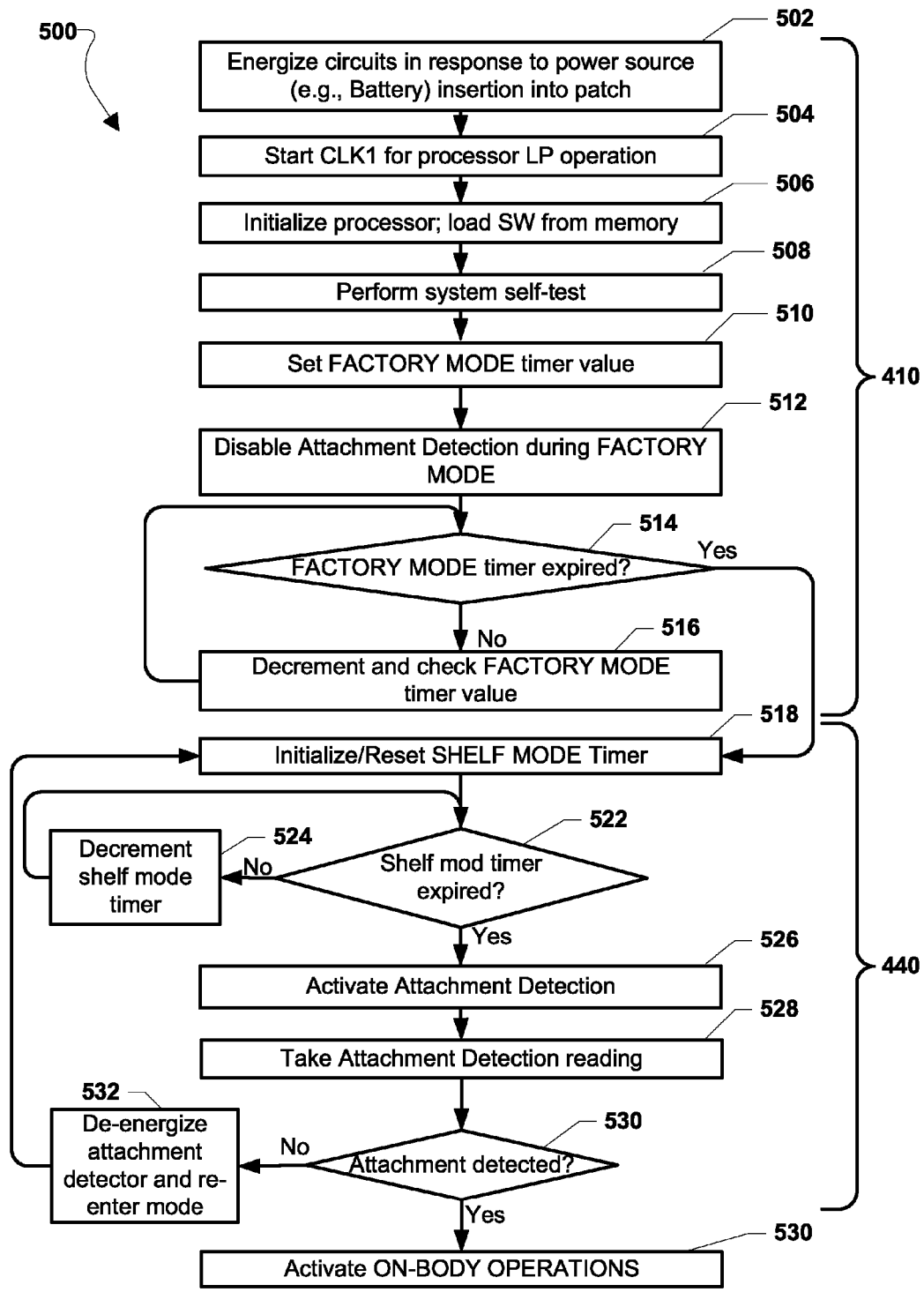
FIG. 5 is a process flow diagram illustrating an embodiment method of performing timing operations and detecting an attachment condition of an electronic patch.

An embodiment method 500 for low power operation during a factory mode 410 and detection operations during a shelf mode 440 is illustrated in FIG. 5. The embodiment method 500 may be implemented in processor-executable instructions executing on the processors or controllers of the electronic patch, embodiments of which are described above.

During manufacturing, the circuits of the electronic patch may be energized in response to the insertion of a power source, such as a battery into the electronic patch in block 502. The insertion of the power source may occur at a known time point in the manufacturing process. In response to the insertion of the power source, the low power clock CLK1 may be started to being in low power processor operation in block 504. The processor may initialize by loading at least a basic or "boot" program from a memory in block 506. The processor may optionally perform a self-test operation, which may be part of the initialization in block 508. In the various embodiments, the self-test may further include a system test for the components of the electronic patch, including the attachment detection device. A factory mode timer value may be set in block 510, by loading a value into the processor. The attachment detection device may be disabled during the factory mode in block 512. Accordingly, the detection capability may be actively tested while in the factory mode such that a detection event is not triggered. For example, a reading of a signal which indicates the RC time constant of the detection sensors may be made and compared against known values to validate proper operation.

The factory mode timer value may be stored in a processor register and the processor may determine if the factory mode timer has expired. In response to determining that the factory mode timer has not expired (i.e., determination block 514="No"), the processor may decrement the factory mode timer in block 516. In response to determining that the factory mode timer has expired (i.e., determination block 514="Yes"), the processor may initialize the shelf mode timer in block 517. By expiration of the factory mode timer and by initializing the shelf mode timer the factory mode 410 may be ended and the shelf mode 440 may begin.

In the shelf mode, a shelf mode timer value may be initialized by loading a timer value from a memory into a processor register and checking after each clock cycle to determine if the shelf mode time has expired. In response to determining that the shelf mode timer has not expired (i.e., determination block 522="No"), the processor may decrement the shelf mode timer in block 524. In response to determining that the shelf mode timer has expired (i.e., determination block 522="Yes"), the processor may activate the attachment detection device in block 526. For example a full cycle clock may be activated and processor operations may be enabled. The attachment detection device and the processor may take an attachment detection reading in block 528. In some embodiments, attachment detection may be accomplished by measuring a capacitance associated with the capacitance sensor to detect the presence of a body. For example, the capacitance may be measured by reading the time constant of a signal applied to or emanating from the attachment detection circuit as described herein above. Measuring capacitance may be accomplished by calculating the capacitance from the time constant or inferring the capacitance by changes in the amount of rise time associated with the signal. In response to detecting that an attachment condition has not occurred (i.e., determination block 530="No"), the processor and the attachment detection device may be de-energized and the low power mode of the shelf mode, such as where the processor may operate from the low power clock, may be reentered in block 532 for another predetermined time interval. By re-entering the low power mode, the full cycle clock may be disabled. Processing may return to block 518, where the shelf mode timer may be reset to loop timer value and processing may continue as described above.

In response to detecting that an attachment condition has occurred (i.e., determination block 530="Yes"), an on-body operations mode may be activated in block 530. Upon activating the on-body operations mode, the full capabilities of the electronic patch may be activated, including sensing and communication functions. In the various embodiments, the low power clock may be operational during at least the factory mode and the shelf mode in order for the processor of the electronic patch to track the time. During full body operation, the low power clock may be optionally disabled. However, in some embodiments, time may be tracked even during full body operations, such as to monitor the remaining battery charge state or estimate the remaining time-to-live as described below with reference to FIG. 6, in which case the low power clock may continue to operate.

As described, being battery-operated, embodiment electronic sensor patches may operate for a limited period of time after activation before the energy stored in the battery is fully consumed. The amount of energy that remains stored in the battery when the electronic patch is applied to a patient will depend upon how much energy was stored in the battery when it was initially installed in the electronic patch (which may be subject to manufacturing variability), as well as the amount of energy consumed while the electronic patch was "on the shelf" prior to use. As described above, monitoring of a capacitance sensor to detect the application of the electronic patch to a patient consumes a small amount of power, and thus the amount of energy stored in the battery when the electronic patch is applied to the patient will decrease over time. Therefore, some capability to determine the remaining power and/or time that the electronic patch has been on the shelf (i.e., operating in the shelf mode) may be beneficial.

Figure 6:
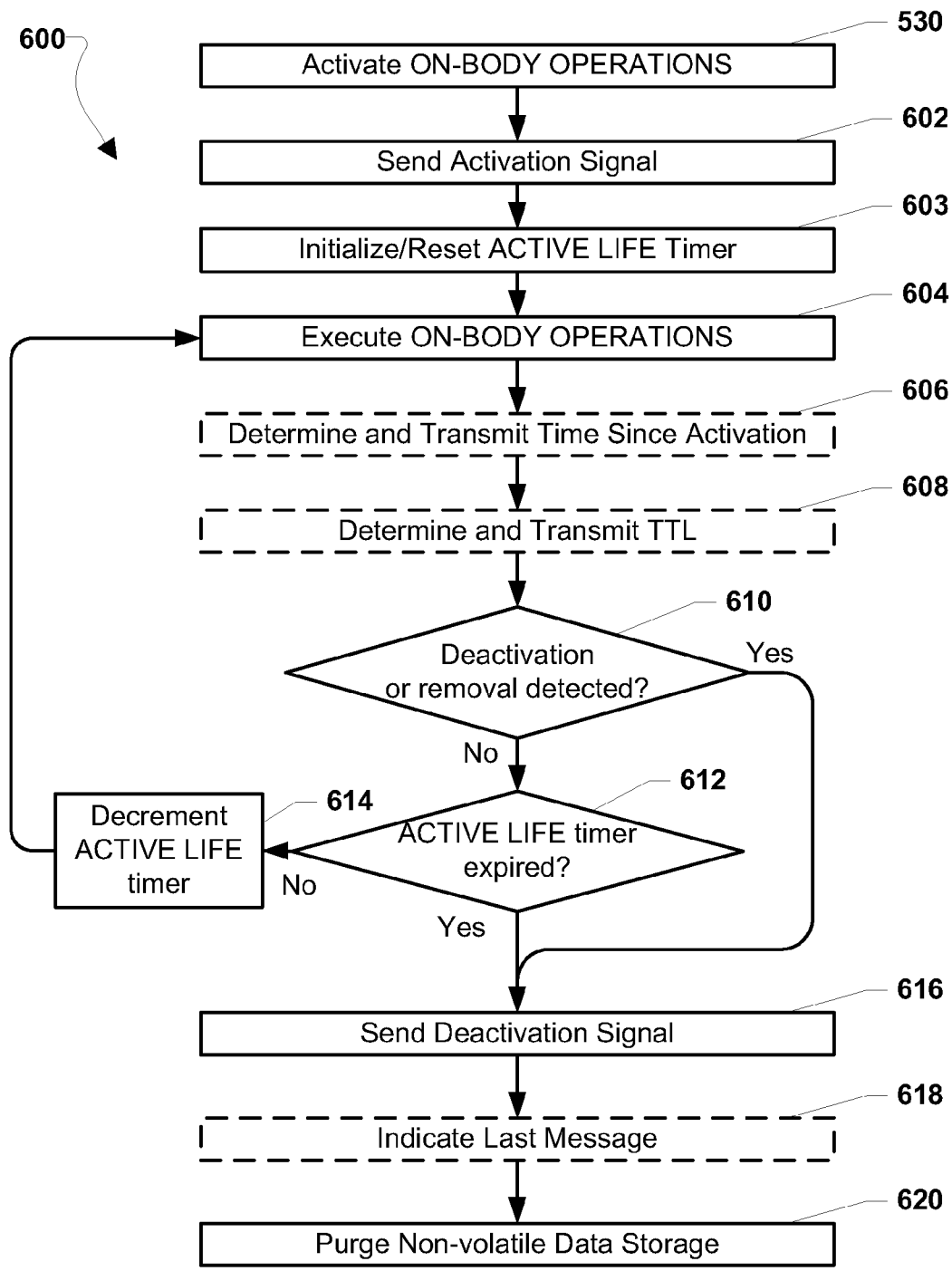
FIG. 6 is a process flow diagram illustrating an embodiment method of performing timing operations for an active life condition of an electronic patch.

To address this, some embodiments include configuring the processor to keep track of the amount of time that the electronic patch has been in the shelf mode and reporting this information in one format or another to a device that communicates with the electronic patch when it is applied to the patient. FIG. 6 illustrates some example operations in method 600 that may be implemented in a processor of an embodiment patch to provide and take action on such information.

In method 600, after or as part of activating on body operations in block 530, the processor of the electronic patch may transmit an activation signal to a receiver device in block 602 that may include an electronic patch identifier (patch ID) and/or other information that a receiver device can use to determine the approximate age or time since the patch's battery was installed. For example, an electronic patch ID may be used to look up the electronic patch in a manufacturing database (e.g., a database accessible via a network or Internet server) that may include the data of manufacture and/or an expiration date. In addition or alternatively, the processor of the electronic patch may transmit a timestamp or other indication of the time since the electronic patch was initially activated (e.g., the time since the battery was installed, the time since the manufacturing mode ended, or the duration that the electronic patch has been in the shelf mode). A device receiving information from the electronic patch may then be able to estimate the amount of power that may be expected to be stored in the battery, and thus estimate a likely duration that the electronic patch will operate on the patient.

The electronic patch processor may also be configured to estimate the amount of time remaining before the battery is expended from on-body operations. For example, upon activation in block 530, the processor may initialize or reset an active life timer in block 603. Such an active life timer may run as long as the electronic patch is in the operating mode to measure the time that the battery is in a high-drain condition while the processor executes on-body operations in block 604. Optionally, the processor may determine the time since activation using this timer in optional block 606. Occasionally as part of the operations in optional block 606, the processor may transmit a time indication indicating the duration of on-body operations. In addition or alternatively, the processor may determine the time-to-live ("TTL" in FIG. 6) and periodically report that in transmissions to a receiver in optional block 608. The processor may calculate an estimate of the time-to-live by monitoring a power consumption rate by the processor or a rate of discharge by the battery, and use that rate to estimate the amount of time before the energy that was stored in the battery at the time of activation is depleted. In some embodiments, the TTL may also or alternatively be calculated by monitoring the voltage of the battery and using that value in a table lookup to obtain an estimated remaining charge level. The estimated remaining charge level can then be compared with the observed discharge rate to obtain an estimate of the remaining time before the battery is fully extended.

In determination block 610, the processor may determine whether the electronic patch has been deactivated, such as by a user action, or removed from the patient. In some embodiments, the processor may detect when the electronic patch is removed from the patient prematurely, such as before the battery has TTL timer has expired or before a predetermined treatment time has passed.

In some embodiments, the processor may maintain a running time to live value based on an initial time-to-live estimation (which itself may be based on the initially determined energy depletion rate and the battery storage level at the time of activation) that is decremented by an active life timer in block 614. For example, in response to determining that the electronic patch has not been deactivated or removed (i.e., determination block 610="No"), the processor may determine whether the active life timer has expired in determination block 612. So long as the electronic patch has not been deactivated and the active life timer has not expired (i.e., determination block 612="No"), the processor may decrement the active life timer in block 614, such as every few milliseconds, seconds, minutes etc. This process may continue as long as the electronic patch is executing on-body operations (e.g., operations in block 604). In some embodiments, the TTL may be visually displayed on the patch itself and/or transmitted to a remote source such that a user can visually see the TTL of a particular patch on a separate device.

Monitoring the remaining TTL in this manner may also enable the processor to perform deactivation operations before the battery is fully expired, such as purging data, deactivating sensors, or performing any other suitable operations to render the electronic patch safe and protect patient privacy (e.g., in order to be in compliance with any health information privacy laws or requirements). For example, in response to either the processor determining that the electronic patch has been deactivated (i.e., determination block 610="Yes"), or that the active life timer has expired (i.e., determination block 612="Yes"), which would indicate that the battery is just about to be expended, the processor may transmit a deactivation signal in block 616 to alert a receiver device that the electronic patch is deactivating. In some embodiments, the electronic sensor patch can transmit a message that can include a patch ID and a time stamp indicating the time of de-activation. Optionally, the electronic sensor patch may also transmit a message indicating that no further messages will be sent in optional block 618.

In embodiments in which the electronic patch is disposable, the processor may purge any non-volatile data storage on the patch to prevent the possibility of exposing any PHI (patient health information) once the patch is disposed, such as in response to the patch being removed from the patient prematurely or deactivated and before the patch is completely de-energized or becomes inoperable. In this manner, compliance with The Health Insurance Portability and Accountability Act of 1996, Pub. L. 104-191, 110 Stat. 1936, (HIPAA) may be achieved. In some embodiments, in response to the electronic patch being deactivated or prematurely removed from the patient and/or once the useful life of the electronic patch expires (e.g., upon active life timer expiry), which may be before the battery of the electronic patch has drained completely, the processor may purge any data contained in a volatile memory or storage device of the patch. The processor may perform data purging by overwriting the memory areas where data is stored, or by removing power to volatile memory to ensure data is not retained by any charge remaining in the battery. In embodiments in which the private information is only stored in volatile RAM, the processor may disconnect the RAM from the battery to erase the data in compliance with various privacy law requirements.

In some embodiments that include a sensor array unit, the processor may send a signal to a hub, or a secondary fixed or mobile device or a remote server before de-energizing or purging the patch data. The signal may inform the hub or secondary device that the patch is being or has been deactivated. The signal may include the patch ID and a time stamp indicating the time of de-activation for record keeping and/or compliance purposes. Additionally, the processor may transmit a final message, such as a message indicating that it is shutting down. However, such a message may not necessarily be received or acknowledged. Therefore, it may not be practical to rely on such a final message, such as for taking important action or conveying important information.

In block 620, the processor may implement a final set of actions to render the electronic patch safe and protect patient data, such as purging all nonvolatile data storage registers so that no patient information remains in memory on the electronic patch. Alternatively, if the patient's private information is only stored in volatile memory (e.g., RAM) on the patch, the processor can drain the battery or disconnect the battery from the memory thereby permanently erasing the private information. By implementing such deactivation operations in response to the processor detecting that the battery is about to expire (e.g., determination block 612="Yes"), the processor is able to retain sufficient power to complete such deactivation operations, which may not be the case if deactivation was caused by full expenditure of the battery.

As described above, the various embodiments provide efficient mechanisms for configuring an electronic patch with a factory mode, a shelf mode, and an on-body operating mode, and for automatically transitioning from the shelf mode to the on-body operating mode, which occurs automatically when the electronic patch is applied to a patient. Thus, in various embodiments a processor of an electronic patch may be configured to execute a method of activating an electronic patch upon application to a patient that includes using a capacitance sensor to determine whether the electronic patch is in close proximity to a body, powering down the processor of the electronic patch to a low-power mode for a predetermined time interval in response to determining that the patch is not in close proximity to a body, and activating the electronic patch in response to determining that the patch is in close proximity to the body. In an embodiment, using a capacitance sensor to determine whether the electronic patch is in close proximity to a body may include measuring capacitance of the capacitance sensor, comparing the measured capacitance of the capacitance sensor to a threshold, and determining that the electronic patch is in close proximity to a body in response to the measured capacitance of the capacitance sensor being more than the threshold.

In an embodiment, using a capacitance sensor to determine whether the electronic patch is in close proximity to a body may include energizing the processor of the electronic patch upon expiration of the threshold time interval, energizing the capacitance sensor, measuring, by the processor, capacitance of the capacitance sensor based on energizing the capacitance sensor, comparing, by the processor, the measured capacitance of the capacitance sensor to a threshold, and determining that the electronic patch is in close proximity to a body in response to the measured capacitance of the capacitance sensor being more than the threshold. In an embodiment, energizing the capacitance sensor may involve applying a voltage from a voltage source to the capacitance sensor or applying a constant current from a constant current source to the capacitance sensor. In an embodiment, powering down a processor of the electronic patch to a low-power mode for a predetermined time interval in response to determining that the patch is not in close proximity to a body may include starting a timer in response determining that the patch is not in close proximity to a body, powering down the processor of the electronic patch to a low-power mode that maintains the time but minimizes power consumption by processor and electronic patch components, determining based on the timer whether the predetermined time interval has elapsed, and leaving the processor in the low-power mode in response to determining based on the timer that the predetermined time interval has not elapsed, in which energizing the processor of the electronic patch upon expiration of the predetermined time interval may include energizing the processor of the electronic patch in response to determining based on the timer that the predetermined time interval has elapsed.

In an embodiment, the processor of the electronic sensor patch may be configured to perform further operations including executing, by the processor, a manufacturing mode in response to connection to a battery power source, wherein while in the manufacturing mode the capacitance sensor is not activated, determining whether a time since the connection to the battery power source exceeds a first time threshold, wherein the first time threshold represents an amount of time that the electronic patch may be handled during manufacturing and testing, and executing, by the processor, a shelf mode in which the capacitive sensor is activated at the predetermined time interval in response to determining that the time since the connection to the battery power source exceeds a first time threshold. In such embodiments, the processor may be configured to perform further operations including determining a duration that the processor has been in the shelf mode in response to activation of the electronic patch, and transmitting an indication of the determined duration that the processor has been in the shelf mode. In such embodiments, the processor may be configured to perform further operations including determining a time-to-live value, and transmitting a time-to-live value. In such embodiments, determining a time-to-live value may include determining an amount of energy stored in the battery upon activation of the electronic patch, determining an energy consumption rate of the electronic patch, and determining the time-to-live based upon the determined amount of energy stored in the battery upon activation of the electronic patch divided by the determined energy consumption rate of the electronic patch minus an amount of time that has transpired since activation of the electronic patch. In such embodiments, the processor may be configure to perform further operations including determining when the determined time-to-live is less than a second time threshold, and deleting data from non-volatile memory of the electronic patch in response to determining that the determined time-to-live is less than a second time threshold.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor-executable instructions or code on a non-transitory computer-readable medium or non-transitory processor-readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments. Various modifications to these embodiments will be readily apparent to those skilled in the art, and the generic principles defined herein may be applied to other embodiments without departing from the scope of embodiments. Thus, the disclosed embodiments are not intended to be limited to only the embodiments shown herein but are to be accorded the widest scope consistent with the following claims and the principles and novel features disclosed herein.

What is claimed is:

1. A method of activating an electronic sensor patch configured to be applied to a patient, comprising:
    using a capacitance sensor to determine whether the electronic sensor patch is in close proximity to a body;
    powering down a processor of the electronic sensor patch to a low-power mode for a predetermined time interval in response to determining that the electronic sensor patch is not in close proximity to a body;
    activating the electronic sensor patch in response to determining that the electronic sensor patch is in close proximity to the body; and
    executing, by the processor, a manufacturing mode in response to connection to a battery power source, wherein while in the manufacturing mode the capacitance sensor is not activated.

2. The method of claim 1, wherein using the capacitance sensor to determine whether the electronic sensor patch is in close proximity to a body comprises:
    measuring a capacitance of the capacitance sensor;
    comparing the measured capacitance of the capacitance sensor to a capacitance threshold; and
    determining that the electronic sensor patch is in close proximity to a body in response to the measured capacitance of the capacitance sensor being more than the capacitance threshold.

3. The method of claim 1, wherein using the capacitance sensor to determine whether the electronic sensor patch is in close proximity to a body comprises:

energizing the processor of the electronic sensor patch upon expiration of the predetermined time interval;
energizing the capacitance sensor;
measuring, by the processor, a capacitance of the capacitance sensor based on energizing the capacitance sensor;
comparing, by the processor, the measured capacitance of the capacitance sensor to a capacitance threshold; and
determining that the electronic sensor patch is in close proximity to a body in response to the measured capacitance of the capacitance sensor being more than the capacitance threshold.

4. The method of claim 3, wherein energizing the capacitance sensor comprises applying to the capacitance sensor one of a voltage from a voltage source, and a constant current from a constant current source.

5. The method of claim 3, wherein powering down the processor of the electronic sensor patch to the low-power mode for the predetermined time interval in response to determining that the electronic sensor patch is not in close proximity to a body comprises:
starting a timer in response determining that the electronic sensor patch is not in close proximity to a body;
powering down the processor of the electronic sensor patch to the low-power mode that monitors the timer and reduces a power consumption by the processor and components of the electronic sensor patch;
determining based on the timer whether the predetermined time interval has elapsed; and
leaving the processor in the low-power mode in response to determining based on the timer that the predetermined time interval has not elapsed,
wherein energizing the processor of the electronic sensor patch upon expiration of the predetermined time interval comprises energizing the processor of the electronic sensor patch in response to determining based on the timer that the predetermined time interval has elapsed.

6. The method of claim 1, further comprising:
determining whether a time since the connection to the battery power source exceeds a first time threshold, wherein the first time threshold represents an amount of time that the electronic sensor patch may be handled during manufacturing and testing; and
executing, by the processor, a shelf mode in which the capacitance sensor is activated at the predetermined time interval in response to determining that the time since the connection to the battery power source exceeds a first time threshold.

7. The method of claim 6, further comprising:
determining a duration that the electronic sensor patch has been in the shelf mode in response to activation of the electronic sensor patch; and
transmitting an indication of the determined duration that the electronic sensor patch has been in the shelf mode.

8. An electronic sensor patch, comprising:
a battery;
a capacitance sensor; and
a processor coupled to the battery and the capacitance sensor, wherein the processor is configured with processor executable instructions to perform operations comprising:
using the capacitance sensor to determine whether the electronic sensor patch is in close proximity to a body;
placing the processor in a low-power mode for a predetermined time interval in response to determining that the electronic sensor patch is not in close proximity to a body;
activating the electronic sensor patch in response to determining that the electronic sensor patch is in close proximity to the body; and
executing, by the processor, a manufacturing mode in response to connection to a battery power source, wherein while in the manufacturing mode the capacitance sensor is not activated.

9. The electronic sensor patch of claim 8, wherein the processor is configured with processor executable instructions to perform operations such that using the capacitance sensor to determine whether the electronic sensor patch is in close proximity to a body comprises:
measuring capacitance of the capacitance sensor;
comparing the measured capacitance of the capacitance sensor to a capacitance threshold; and
determining that the electronic sensor patch is in close proximity to a body in response to the measured capacitance of the capacitance sensor being more than the capacitance threshold.

10. The electronic sensor patch of claim 8, wherein the processor is configured with processor executable instructions to perform operations such that using the capacitance sensor to determine whether the electronic sensor patch is in close proximity to a body comprises:
energizing the processor of the electronic sensor patch upon expiration of the predetermined time interval;
energizing the capacitance sensor;
measuring capacitance of the capacitance sensor based on energizing the capacitance sensor;
comparing the measured capacitance of the capacitance sensor to a capacitance threshold; and
determining that the electronic sensor patch is in close proximity to a body in response to the measured capacitance of the capacitance sensor being more than the capacitance threshold.

11. The electronic sensor patch of claim 10, wherein the processor is configured with processor-executable instructions such that energizing the capacitance sensor comprises applying to the capacitance sensor one of a voltage from a voltage source, and a constant current from a constant current source.

12. The electronic sensor patch of claim 10, wherein the processor is configured with processor-executable instructions such that powering down the processor of the electronic sensor patch to the low-power mode for the predetermined time interval in response to determining that the electronic sensor patch is not in close proximity to a body comprises:
starting a timer in response determining that the electronic sensor patch is not in close proximity to a body;
powering down the processor of the electronic sensor patch to the low-power mode that monitors the timer but minimizes power consumption by the processor and components of the electronic sensor patch;
determining based on the timer whether the predetermined time interval has elapsed; and
leaving the processor in the low-power mode in response to determining based on the timer that the predetermined time interval has not elapsed,
wherein energizing the processor of the electronic sensor patch upon expiration of the predetermined time interval comprises energizing the processor of the electronic sensor patch in response to determining based on the timer that the predetermined time interval has elapsed.

13. The electronic sensor patch of claim 8, wherein the processor is configured with processor-executable instructions to perform operations further comprising:
   determining whether a time since the connection to the battery power source exceeds a first time threshold, wherein the first time threshold represents an amount of time that the electronic sensor patch may be handled during manufacturing and testing; and
   executing a shelf mode in which the capacitance sensor is activated at the predetermined time interval in response to determining that the time since the connection to the battery power source exceeds a first time threshold.

14. The electronic sensor patch of claim 13, wherein the processor is configured with processor-executable instructions to perform operations further comprising:
   determining a duration that the electronic sensor patch has been in the shelf mode in response to activation of the electronic sensor patch; and
   transmitting an indication of the determined duration that the electronic sensor patch has been in the shelf mode.

15. An electronic sensor patch, comprising:
   a battery;
   a capacitance sensor;
   means for using the capacitance sensor to determine whether the electronic sensor patch is in close proximity to a body;
   means for placing the electronic sensor patch in a low-power mode for a predetermined time interval in response to determining that the electronic sensor patch is not in close proximity to a body;
   means for activating the electronic sensor patch in response to determining that the electronic sensor patch is in close proximity to the body; and
   means for executing a manufacturing mode in response to connection to a battery power source, wherein while in the manufacturing mode the capacitance sensor is not activated.

16. The electronic sensor patch of claim 15, wherein means for using the capacitance sensor to determine whether the electronic sensor patch is in close proximity to a body comprises:
   means for measuring a capacitance of the capacitance sensor;
   means for comparing the measured capacitance of the capacitance sensor to a capacitance threshold; and
   means for determining that the electronic sensor patch is in close proximity to a body in response to the measured capacitance of the capacitance sensor being more than the capacitance threshold.

17. The electronic sensor patch of claim 15, wherein means for using the capacitance sensor to determine whether the electronic sensor patch is in close proximity to a body comprises:
   means for energizing the capacitance sensor upon expiration of the predetermined time interval;
   means for measuring a capacitance of the capacitance sensor based on energizing the capacitance sensor;
   means for comparing the measured capacitance of the capacitance sensor to a capacitance threshold; and
   means for determining that the electronic sensor patch is in close proximity to a body in response to the measured capacitance of the capacitance sensor being more than the capacitance threshold.

18. The electronic sensor patch of claim 17, wherein means for energizing the capacitance sensor comprises means for applying to the capacitance sensor one of a voltage from a voltage source, and a constant current from a constant current source.

19. The electronic sensor patch of claim 17, wherein the means for placing the electronic sensor patch in the low-power mode for the predetermined time interval in response to determining that the electronic sensor patch is not in close proximity to a body comprises:
   means for starting a timer in response determining that the electronic sensor patch is not in close proximity to a body;
   means for powering down the electronic sensor patch to the low-power mode that maintains the timer but minimizes power consumption by components of the electronic sensor patch;
   means for determining based on the timer whether the predetermined time interval has elapsed; and
   means for leaving the electronic sensor patch in the low-power mode in response to determining based on the timer that the predetermined time interval has not elapsed,
   wherein the means for energizing the capacitance sensor upon expiration of the predetermined time interval comprises means for energizing the capacitance sensor in response to determining based on the timer that the predetermined time interval has elapsed.

20. The electronic sensor patch of claim 15, further comprising:
   means for determining whether a time since the connection to the battery power source exceeds a first time threshold, wherein the first time threshold represents an amount of time that the electronic sensor patch may be handled during manufacturing and testing; and
   means for executing a shelf mode in which the capacitance sensor is activated at the predetermined time interval in response to determining that the time since the connection to the battery power source exceeds a first time threshold.

21. The electronic sensor patch of claim 20, further comprising:
   means for determining a duration that the electronic sensor patch has been in the shelf mode in response to activation of the electronic sensor patch; and
   means for transmitting an indication of the determined duration that the electronic sensor patch has been in the shelf mode.

22. A non-transitory processor-readable storage medium having stored thereon processor-executable instructions configured to cause a processor of an electronic sensor patch to perform operations comprising:
   using a capacitance sensor to determine whether the electronic sensor patch is in close proximity to a body;
   powering down the processor of the electronic sensor patch to a low-power mode for a predetermined time interval in response to determining that the electronic sensor patch is not in close proximity to a body;
   activating the electronic sensor patch in response to determining that the electronic sensor patch is in close proximity to the body; and
   executing a manufacturing mode in response to connection to a battery power source, wherein while in the manufacturing mode the capacitance sensor is not activated.

23. The non-transitory processor-readable storage medium of claim 22, wherein the stored processor executable instructions are configured to cause the processor perform operations such that using the capacitance sensor to determine whether the electronic sensor patch is in close proximity to a body comprises:
measuring capacitance of the capacitance sensor;
comparing the measured capacitance of the capacitance sensor to a capacitance threshold; and
determining that the electronic sensor patch is in close proximity to a body in response to the measured capacitance of the capacitance sensor being more than the capacitance threshold.

24. The non-transitory processor-readable storage medium of claim 22, wherein the stored processor executable instructions are configured to cause the processor perform operations such that using the capacitance sensor to determine whether the electronic sensor patch is in close proximity to a body comprises:
energizing the processor of the electronic sensor patch upon expiration of the predetermined time interval;
energizing the capacitance sensor;
measuring capacitance of the capacitance sensor based on energizing the capacitance sensor;
comparing the measured capacitance of the capacitance sensor to a capacitance threshold; and
determining that the electronic sensor patch is in close proximity to a body in response to the measured capacitance of the capacitance sensor being more than the capacitance threshold.

25. The non-transitory processor-readable storage medium of claim 24, wherein the stored processor-executable instructions are configured to cause the processor to perform operations such that energizing the capacitance sensor comprises applying to the capacitance sensor one of a voltage from a voltage source, and a constant current from a constant current source.

26. The non-transitory processor-readable storage medium of claim 24, wherein the stored processor-executable instructions are configured to cause the processor to perform operations such that powering down the processor of the electronic sensor patch to the low-power mode for the predetermined time interval in response to determining that the electronic sensor patch is not in close proximity to a body comprises:
starting a timer in response determining that the electronic sensor patch is not in close proximity to a body;
powering down the processor of the electronic sensor patch to the low-power mode that monitors the timer and reduces a power consumption by the processor and components of the electronic sensor patch;
determining based on the timer whether the predetermined time interval has elapsed; and
leaving the processor in the low-power mode in response to determining based on the timer that the predetermined time interval has not elapsed,
wherein energizing the processor of the electronic sensor patch upon expiration of the predetermined time interval comprises energizing the processor of the electronic sensor patch in response to determining based on the timer that the predetermined time interval has elapsed.

27. The non-transitory processor-readable storage medium of claim 22, wherein the stored processor-executable instructions are configured to cause the processor to perform operations further comprising:
determining whether a time since the connection to the battery power source exceeds a first time threshold, wherein the first time threshold represents an amount of time that the electronic sensor patch may be handled during manufacturing and testing; and
executing a shelf mode in which the capacitance sensor is activated at the predetermined time interval in response to determining that the time since the connection to the battery power source exceeds a first time threshold.

28. The non-transitory processor-readable storage medium of claim 27, wherein the stored processor-executable instructions are configured to cause the electronic sensor patch to perform operations further comprising:
determining a duration that the processor has been in the shelf mode in response to activation of the electronic sensor patch; and
transmitting an indication of the determined duration that the electronic sensor patch has been in the shelf mode.

29. A method of deactivating an electronic sensor patch configured to be applied to a patient, comprising:
activating an timer in response to activation of the electronic sensor patch;
determining, by a processor of the electronic sensor patch, whether the timer has expired; and
deactivating, by the processor, the electronic sensor patch in response to determining that the timer has expired, wherein deactivating the electronic sensor patch includes purging data stored in memory of the electronic sensor patch.

30. The method of claim 29, further comprising:
using a capacitance sensor to determine whether the electronic sensor patch is in close proximity to a body; and
activating the electronic sensor patch in response to determining that the electronic sensor patch is in close proximity to the body.

31. The method of claim 30, further comprising executing an on-body operations mode to perform one or more on-body operations in response to activating the electronic sensor patch.

32. The method of claim 31, wherein the one or more on-body operations include at least one member of the group consisting of: a sensing operation; and a communication operation.

33. The method of claim 30, further comprising powering down the processor of the electronic sensor patch to a low-power mode for a predetermined time interval in response to determining that the electronic sensor patch is not in close proximity to a body.

34. The method of claim 29, further comprising sending a deactivation signal in response to determining that the timer has expired.

35. The method of claim 34, wherein the deactivation signal indicates that the electronic sensor patch will be deactivated.

36. The method of claim 29, wherein purging the data stored in the memory of the electronic sensor patch comprises at least one member of the group consisting of:
disconnecting power to the memory; and overwriting the data stored in the memory.

37. The method of claim 29, wherein determining whether the timer has expired comprises determining that the active life timer has expired when the value of the timer is one of: zero; equal to an active life time value; and less than the active life time value.

38. An electronic sensor patch, comprising:
a battery;
a timer;
a capacitance sensor; and a processor coupled to the battery, the timer, and the capacitance sensor, wherein the processor is configured with processor-executable instructions to perform operations comprising:
  activating the timer in response to activation of the electronic sensor patch;
  determining whether the timer has expired; and
  deactivating the electronic sensor patch in response to determining that the timer has expired, wherein deactivating the electronic sensor patch includes purging data stored in memory of the electronic sensor patch.

39. The electronic sensor patch of claim 38, wherein the processor is configured with processor executable-instructions to perform operations further comprising:
  using the capacitance sensor to determine whether the electronic sensor patch is in close proximity to a body; and
  activating the electronic sensor patch in response to determining that the electronic sensor patch is in close proximity to the body.

40. The electronic sensor patch of claim 39, wherein the processor is configured with processor-executable instructions to perform operations further comprising:
  executing an on-body operations mode to perform one or more on-body operations in response to activating the electronic sensor patch.

41. The electronic sensor patch of claim 40, further comprising:
  a radio module coupled to the processor; and
  one or more sensors coupled to the processor,
  wherein the processor is configured with processor executable instructions to perform operations such that the one or more on-body operations include at least one member of the group consisting of: sensing operations using the one or more sensors; and a communication operation using the radio module.

42. The electronic sensor patch of claim 39, wherein the processor is configured with processor executable instructions to perform operations further comprising:
  powering down the processor to a low-power mode for a predetermined time interval in response to determining that the electronic sensor patch is not in close proximity to a body.

43. The electronic sensor patch of claim 38, further comprising a radio module coupled to the processor, wherein the processor is configured with processor executable instructions to perform operations further comprising sending a deactivation signal using the radio module in response to determining that the timer has expired.

44. The electronic sensor patch of claim 43, wherein the processor is configured with processor executable instructions to perform operations such the deactivation signal indicates that the electronic sensor patch will be deactivated.

45. The electronic sensor patch of claim 38, wherein the processor is configured with processor executable instructions to perform operations such that purging the data stored in the memory comprises at least one member of the group consisting of:
  disconnecting power to the memory; and overwriting the data stored in the memory.

46. The electronic sensor patch of claim 38, wherein the processor is configured with processor executable instructions to perform operations such that determining whether the timer has expired comprises determining that the timer has expired when the value of the timer is one of: zero; equal to an active life time value; and less than the time value.

47. An electronic sensor patch, comprising:
  a battery;
  an timer;
  a capacitance sensor; and
  means for activating the timer in response to activation of the electronic sensor patch;
  means for determining whether the timer has expired; and
  means for deactivating the electronic sensor patch in response to a determination that the timer has expired, wherein deactivating the electronic sensor patch includes purging data stored in memory of the electronic sensor patch.

48. The electronic sensor patch of claim 47, further comprising:
  means for using the capacitance sensor to determine whether the electronic sensor patch is in close proximity to a body; and
  means for activating the electronic sensor patch in response to determining that the electronic sensor patch is in close proximity to the body.

49. The electronic sensor patch of claim 48, further comprising:
  means for executing an on-body operations mode to perform one or more on-body operations in response to activation of the electronic sensor patch.

50. The electronic sensor patch of claim 48, wherein means for executing one or more on-body operations comprises at least one member of the group consisting of: means for executing a sensing operation; and means for executing a communication operation.

51. The electronic sensor patch of claim 48, further comprising:
  means for powering down the electronic sensor patch to a low-power mode for a predetermined time interval in response to a determination that the electronic sensor patch is not in close proximity to a body.

52. The electronic sensor patch of claim 47, further comprising means for sending a deactivation signal in response to a determination that the timer has expired.

53. The electronic sensor patch of claim 52, wherein the deactivation signal indicates that the electronic sensor patch will be deactivated.

54. The electronic sensor patch of claim 47, wherein the purging of the data stored in the memory of the electronic sensor patch comprises at least one member of the group consisting of: means for disconnecting power to the memory; and means for overwriting data stored in the memory.

55. The electronic sensor patch of claim 47, wherein means for determining whether the timer has expired comprises means for determining that the timer has expired when the value of the timer is one of: zero; equal to an active life time value; and less than the active life time value.

56. A non-transitory processor-readable storage medium having stored thereon processor-executable instructions configured to cause a processor of an electronic sensor patch to perform operations comprising:
  activating an timer in response to activation of the electronic sensor patch;
  determining whether the timer has expired; and
  deactivating the electronic sensor patch in response to determining that the timer has expired, wherein deactivating the electronic sensor patch includes purging data stored in memory of the electronic sensor patch.

57. The non-transitory processor-readable storage medium of claim 56, wherein the stored processor-executable instructions are configured to cause the processor of the electronic sensor patch to perform operations further comprising:

using a capacitance sensor to determine whether the electronic sensor patch is in close proximity to a body; and activating the electronic sensor patch in response to determining that the electronic sensor patch is in close proximity to the body.

58. The non-transitory processor-readable storage medium of claim 57, wherein the stored processor-executable instructions are configured to cause the processor of the electronic sensor patch to perform operations further comprising:

executing an on-body operations mode to perform one or more on-body operations in response to activating the electronic sensor patch.

59. The non-transitory processor-readable storage medium of claim 58, wherein the stored processor-executable instructions are configured to cause the processor of the electronic sensor patch to perform operations such that the one or more on-body operations include at least one member of the group consisting of: one or more sensing operations; and a communication operation.

60. The non-transitory processor-readable storage medium of claim 57, wherein the stored processor-executable instructions are configured to cause the processor of the electronic sensor patch to perform operations further comprising:

powering down the processor to a low-power mode for a predetermined time interval in response to determining that the electronic sensor patch is not in close proximity to a body.

61. The non-transitory processor-readable storage medium of claim 56, wherein the stored processor-executable instructions are configured to cause the processor of the electronic sensor patch to perform operations further comprising sending a deactivation signal in response to determining that the timer has expired.

62. The non-transitory processor-readable storage medium of claim 61, wherein the stored processor-executable instructions are configured to cause the processor of the electronic sensor patch to perform operations such that sending the deactivation signal indicates that the electronic sensor patch will be deactivated.

63. The non-transitory processor-readable storage medium of claim 56, wherein the stored processor-executable instructions are configured to cause the processor of the electronic sensor patch to perform operations such that purging the data stored in the memory of the electronic sensor patch comprises at least one member of the group consisting of:

disconnecting power to the memory; and overwriting the data stored in the memory.

64. The non-transitory processor-readable storage medium of claim 56, wherein the stored processor-executable instructions are configured to cause the processor of the electronic sensor patch to perform operations such that determining whether the timer has expired comprises determining that the timer has expired when the value of the timer is one of: zero; equal to an active life time value; and less than the active life time value.

* * * * *